(12) United States Patent
Wakamiya et al.

(10) Patent No.: US 8,425,839 B2
(45) Date of Patent: Apr. 23, 2013

(54) SAMPLE ANALYZER

(75) Inventors: Yuji Wakamiya, Kobe (JP); Tomohiro Okuzaki, Himeji (JP); Hisato Takehara, Kobe (JP)

(73) Assignee: Sysmex Corporation, Kobe (JP)

( * ) Notice: Subject to any disclaimer, the term of this patent is extended or adjusted under 35 U.S.C. 154(b) by 1108 days.

(21) Appl. No.: 12/079,794

(22) Filed: Mar. 28, 2008

(65) Prior Publication Data

US 2008/0240991 A1 Oct. 2, 2008

(30) Foreign Application Priority Data

Mar. 30, 2007 (JP) ................................ 2007-093070
Jan. 25, 2008 (JP) ................................ 2008-015538

(51) Int. Cl.
*G01N 15/06* (2006.01)
*G01N 33/00* (2006.01)
*G01N 33/48* (2006.01)

(52) U.S. Cl.
USPC ............... 422/68.1; 422/50; 422/63; 422/64; 422/66; 422/67; 422/81; 422/82.01; 422/82.05; 436/43; 436/47; 436/54; 436/63; 436/66; 436/68; 436/69; 436/70; 436/71; 436/174; 436/180

(58) Field of Classification Search .................... 422/50, 422/63, 64, 65, 66, 67, 81, 82.01, 82.05, 422/68.1; 436/43, 47, 54, 63, 66, 67, 68, 436/69, 70, 71, 174, 180

See application file for complete search history.

(56) References Cited

U.S. PATENT DOCUMENTS

2005/0053521 A1* 3/2005 Hirayama ...................... 422/67

FOREIGN PATENT DOCUMENTS

JP 2005-121492 5/2005

* cited by examiner

*Primary Examiner* — Brian J Sines
(74) *Attorney, Agent, or Firm* — Brinks Hofer Gilson & Lione

(57) ABSTRACT

A sample analyzer is disclosed that comprising: a first reagent container to hold a first reagent container with a first record section which contains a first reagent management information; a second reagent container holder to hold a second reagent container with a second record section which contains a second reagent management information; a first information reader; a second information reader; a registration section for registering the combination of the first reagent and the second reagent based on the first reagent management information; a measurement section for conducting a measurement of a predetermined analysis item by using the first reagent and the second reagent corresponding to the combination registered by the registration section; and a processing section for processing a measurement result obtained by the measurement section, and for obtaining an analysis result of the sample.

19 Claims, 22 Drawing Sheets

SAMPLE ANALYZER

RELATED APPLICATIONS

This application claims priority under 35 U.S.C. §119 to Japanese Patent Application No. JP2007-093070 filed Mar. 30, 2007 and Japanese Patent Application No. JP2008-015538 filed Jan. 25, 2008, the entire contents of which are hereby incorporated by reference.

TECHNICAL FIELD

The present invention relates to a sample analyzer, in particular, to a sample analyzer for analyzing a predetermined analysis items by using at least a first reagent and a second reagent.

BACKGROUND

A sample analyzer for analyzing a predetermined analysis item by using a first reagent and a second reagent is conventionally known (e.g., Japanese Laid-Open Patent Publication No. 2005-121492).

In the sample analyzer disclosed in Japanese Laid-Open Patent Publication No. 2005-121492, analysis is performed by using a cassette in which a plurality of reagent containers respectively accommodating a plurality of reagents necessary for analyzing the analyzing item is fixed to each other when analyzing the analysis item analyzed by using a plurality of reagents. The cassette is held in a reagent disc. Conventionally, analysis is sometimes performed by using a reagent that needs to be performed with a predetermined process such as stirring and a reagent that does not need to be performed with the predetermined process depending on the analysis item. If the predetermined process is performed on the reagent that does not need to be performed with the predetermined process, the measurement result may be adversely affected.

It is easy to manage the plurality of reagents contained in the cassette as the reagent necessary for the same analysis item in the sample analyzer disclosed in Japanese Laid-Open Patent Publication No. 2005-121492 since analysis is performed by using the cassette in which the plurality of reagent containers are fixed to each other. However, there is a disadvantage that it is difficult to perform a predetermined process only on the reagent that needs to be performed with the predetermined process.

It can be considered to hold a reagent container for accommodating the reagent that needs to be performed with a predetermined process and a reagent container for accommodating the reagent that does not need to be performed with a predetermined process in different holding sites from each other. In this case, it can be easy to perform the predetermined process only on the reagent that needs to be performed with the predetermined process. However, there is a problem that it is difficult to manage the reagent that needs to be performed with the predetermined process and the reagent that does not need to be performed with the predetermined process as the reagent used in the same analysis item.

SUMMARY

The scope of the present invention is defined solely by the appended claims, and is not affected to any degree by the statements within this summary.

A first sample analyzer for analyzing a sample by using a first reagent and a second reagent embodying features of the present invention includes: a first reagent container holder capable of holding a first reagent container, wherein the first reagent container accommodates the first reagent, and comprises a first record section which contains a first reagent management information; a second reagent container holder capable of holding a second reagent container, wherein the second reagent container accommodates the second reagent, and comprises a second record section which contains a second reagent management information; a first information reader for reading the first reagent management information from the first record section; a second information reader for reading the second reagent management information from the second record section; a registration section for registering the combination of the first reagent and the second reagent based on the first reagent management information read by the first information reader and the second reagent management information read by the second information reader; a measurement section for conducting a measurement of a predetermined analysis item by using the first reagent and the second reagent corresponding to the combination registered by the registration section; and a processing section for processing a measurement result obtained by the measurement section, and for obtaining an analysis result of the sample.

A second sample analyzer for analyzing a sample by using a first reagent and a second reagent embodying features of the present invention includes: a first reagent container holder capable of holding a first reagent container, wherein the first reagent container accommodates the first reagent, and comprises a first record section recorded with first reagent management information used in managing the first reagent; a second reagent container holder capable of holding a second reagent container, wherein the second reagent container accommodates the second reagent, and comprises a second record section recorded with second reagent management information used in managing the second reagent; a first information reader for reading the first reagent management information from the first record section of the first reagent container; a second information reader for reading the second reagent management information from the second record section of the second reagent container; a determining section for determining whether or not the first reagent management information read by the first information reader and the second reagent management information read by the second information reader correspond; a measurement section for conducting a measurement of a predetermined analysis item by using the first reagent and the second reagent when determined that the first reagent management information and the second reagent management information correspond by the determining section; a processing section for processing a measurement result obtained by the measurement section, and for obtaining an analysis result of the sample; and a measurement prohibiting section for prohibiting measurement of the predetermined analysis item by the measurement section by using the first reagent and the second reagent when determined that the first reagent management information and the second reagent information do not correspond by the determining section.

DETAILED DESCRIPTION OF THE PREFERRED EMBODIMENTS

The embodiments embodying the present invention will be described below based on the drawings.

The overall configuration of an immunological analyzer 1 according to one embodiment of the present invention will be now described with reference to FIGS. 1 to 6.

The immunological analyzer 1 according to one embodiment of the present invention is an apparatus for carrying out examinations on various items such as hepatitis B, hepatitis C, tumor marker, and thyroid hormone by using sample such as blood. In the immunological analyzer 1, capture antibody (R1 reagent) is bonded to the antigen contained in the sample such as blood, which is the measuring object. The magnetic particles (R2 reagent) are then bonded to the capture antibody (R1 reagent). The complex including the antigen, and the capture antibody and the magnetic particles bound to the antigen are attracted to a magnet (not shown) of a BF (Bound Free) separator 14 (see FIGS. 1 and 2) to remove the R1 reagent containing non-reactive (free) capture antibody. A labeled antibody (R3 reagent) is bonded to the antigen bound with magnetic particles. Thereafter, the complex including the antigen and the bound magnetic particles, and the labeled antibody are attracted to a magnet of a BF separator 14 to remove a R3 reagent containing non-reactive (free) labeled antibody. The complex of the magnetic particles, the antigen, and the labeled antibody is dispersed in dispersion liquid (R4 reagent). Furthermore, a light emitting substrate (R5 reagent) that emits light in the reaction process with the labeled antibody is added. The light emitting amount generated through the reaction of the labeled antibody and the light emitting substrate is measured. After such processes, the antigen or the antibody contained in the sample that bonds with the labeled antibody is quantitatively measured. Thus, in the immunological analyzer 1, measurement is conducted by using five types of reagents R1 to R5. Among the five types of reagents, R4 reagent and R5 reagent are commonly used for each measurement item. R1 reagent, R2 reagent and R3 reagent are reagents dedicated for every measurement item. In the embodiment, R1/R3 reagent and R2 reagent are held in different places, and R1/R3 reagent and R2 reagent used in the same measurement item are managed as a set.

Figure 1:
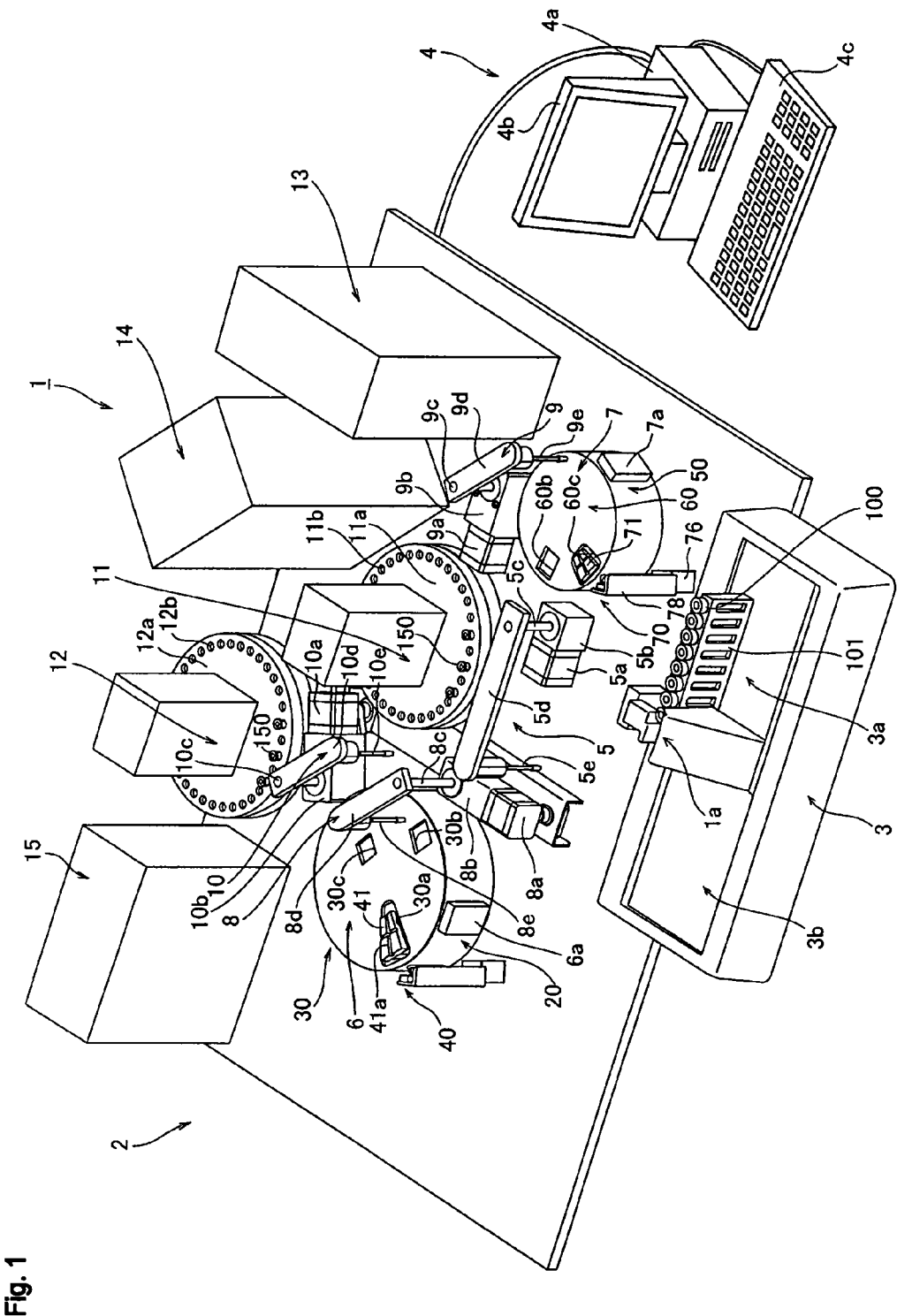
FIG. 1 is a perspective view showing an overall configuration of an immunological analyzer according to one embodiment of the present invention.
Figure 2:
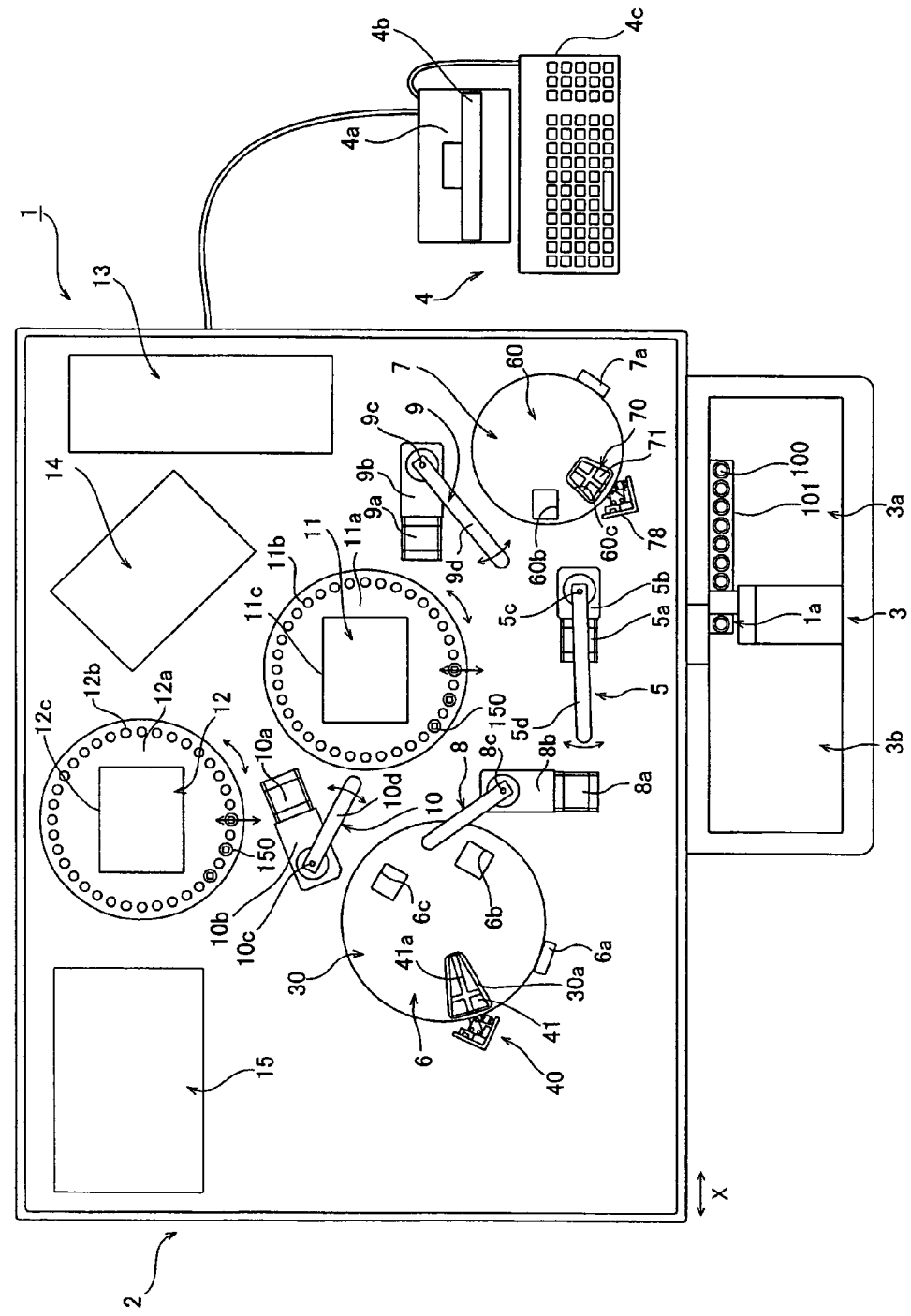
FIG. 2 is a plan view of the immunological analyzer shown in FIG. 1.
Figure 3:
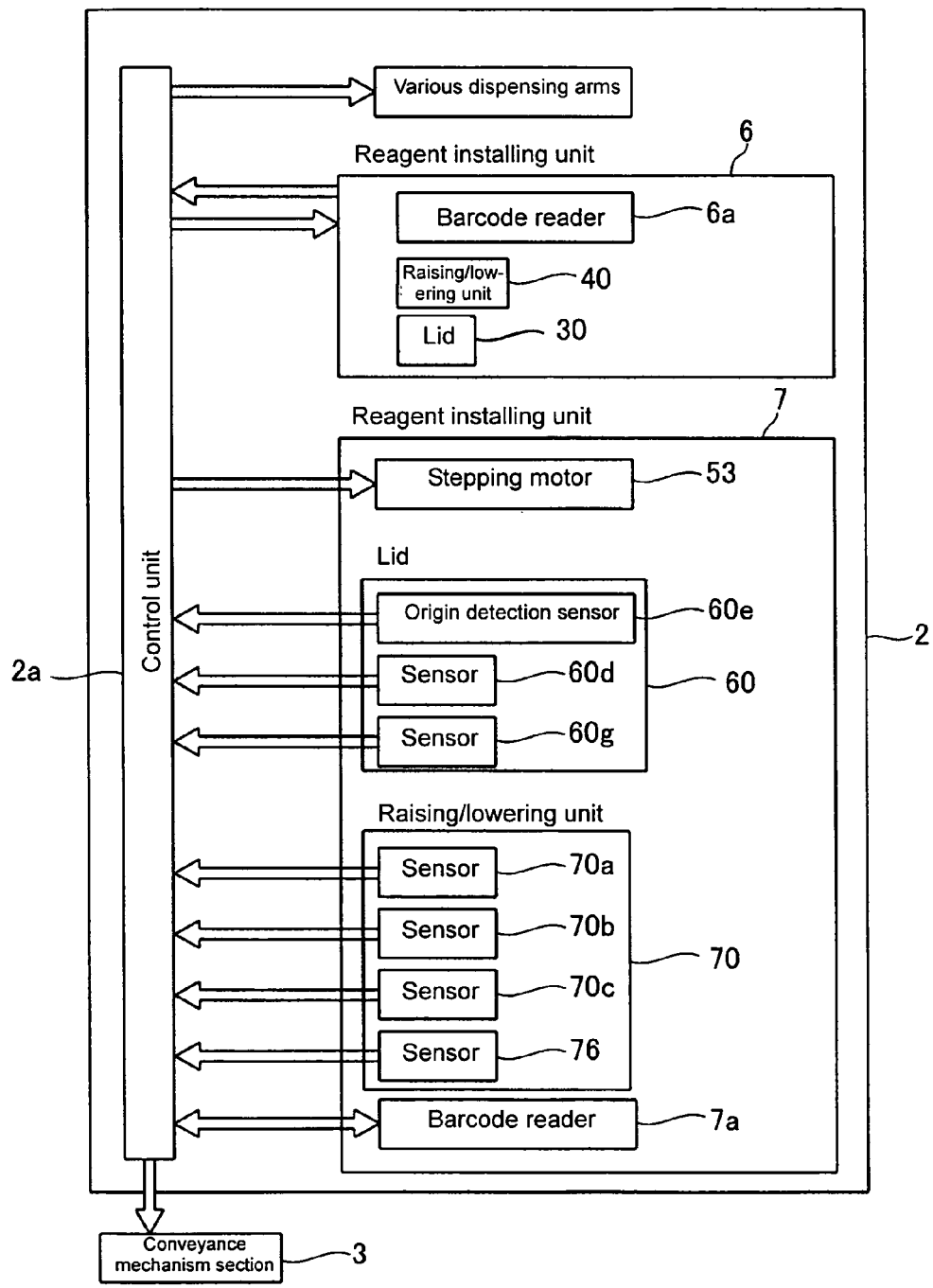
FIG. 3 is a block diagram including a control unit of a measurement mechanism section of the immunological analyzer according to one embodiment of the present invention.

As shown in FIGS. 1 and 2, the immunological analyzer 1 includes a measurement mechanism section 2, a sample conveyance section (sampler) 3 arranged on the front surface side of the measurement mechanism section 2, and a control device 4 including PC (personal computer) electrically connected to the measurement mechanism section 2. The measurement mechanism section 2 is configured by a sample dispensing arm 5, reagent installing units 6 and 7, reagent dispensing arms 8, 9, and 10, a primary reaction unit 11 and a secondary reaction unit 12, a cuvette supplying unit 13, a BF separator 14, and a detector 15. As shown in FIG. 3, each mechanism (various dispensing arms, reagent installing unit 6, and reagent installing unit 7, and the like) in the measurement mechanism section 2 are controlled by a control unit 2a arranged in the measurement mechanism section 2. Specifically, the control unit 2a receives signals of various sensors (sensors 60d, 60g and origin detection sensor 60e contained in a lid 60, sensors 70a, 70b and 70c contained in a raising/lowering unit 70, and the like) arranged in the reagent installing unit 7, and controls the drive of various driving sources (stepping motors 53 and 76, and the like) arranged in the reagent installing unit 7. Similarly, the control unit 2a controls a lid 30 and a raising/lowering unit 40 of the reagent installing unit 6. Reagent information of the reagent installed in the reagent installing units 6 and 7 are read by barcode readers 6a and 7a, and input to the control unit 2a. The conveyance mechanism section 3 is also controlled by the control unit 2a. The various dispensing arms, various sensors, and various driving sources will be described in detail below.

Figure 4:
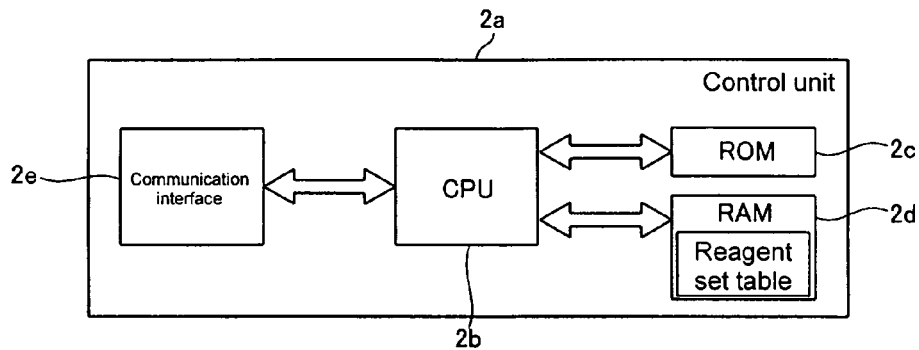
FIG. 4 is a block diagram showing a configuration of the control unit of the measurement mechanism section shown in FIG. 3.

As shown in FIG. 4, the control unit 2a is mainly configured by a CPU 2b, a ROM 2c, a RAM 2d, and a communication interface 2e.

The CPU 2b can execute computer programs stored in the ROM 2c and the computer programs read by the RAM 2d. The ROM 2c stores computer programs executed by the CPU 2b, data used in executing the computer program, and the like.

The RAM 2d is used to read out the computer program stored in the ROM 2c. In executing the computer program, the RAM 2d is used as a work region of the CPU 2b. The RAM 2d stores reagent set table including reagent information of each reagent installed in the reagent installing units 6 and 7, position information in the reagent installing units 6 and 7 of each reagent. The reagent set table contains, for every reagent installed in the reagent installing units 6 and 7, position information in the reagent installing unit 6 or 7 of the reagent, measurement item, type of reagent, lot number, serial number of a reagent-containing assembly to be described below, measurable number of times at current point, expiration date, presence or absence of opponent configuring a set, and serial number of the opponent reagent configuring the set. The reagent set table is created at the time of activation of the apparatus, and is sequentially updated in time of measurement and replacement or retrieval of the reagent. The creating process and the updating process of the reagent set table will be described in detail below.

The communication interface 2e is connected to the control device 4, transmits optical information (data of light emission amount generated by reaction of the labeled antibody and light emitting substrate) of the sample to the control device 4, and receives signals from the control unit 4a of the control device 4. The communication interface 2e has a function of transmitting a command from the CPU 2b for driving each unit of the conveyance mechanism section 3 and the measurement mechanism section 2.

As shown in FIGS. 1 and 2, the sample conveyance section 3 is configured to convey a rack 101 mounted with a plurality of test tubes 100 accommodating the sample to a position corresponding to an aspirating position 1a where the sample dispensing arm 5 aspirates the sample. The sample conveyance section 3 includes a rack set part 3a for setting the rack 101 in which the test tubes 100 accommodating non-processed sample are mounted, and a rack storing part 3b for storing the rack 101 in which the test tubes 100 accommodating the dispensing processed sample are mounted. The test tube 100 accommodating the non-processed sample is conveyed to a position corresponding to the aspirating position 1a of the sample dispensing arm 5, so that the sample dispensing arm 5 aspirates the sample such as blood in the test tube 100, and thereafter, the rack 101 mounted with the test tube 100 is stored in the rack storing part 3b.

The control device 4 (FIG. 1) comprises a personal computer (PC), and includes a control unit 4a including such as CPU, ROM, and RAM, a display unit 4b and a keyboard 4c. The display unit 4b is arranged to display analysis result obtained by analyzing data of digital signals transmitted from a detector 15. The display unit 4b can also display arrangement state of each reagent in the reagent installing units 6 and 7, list of measurement items that can be measured when the reagent installed in the reagent installing unit 6 and the reagent installed in the reagent installing unit 7 configure a set, and the like. In the present embodiment, instruction of replacement and retrieval of the reagent-containing assembly to be described below can be made in the control device 4.

Figure 5:
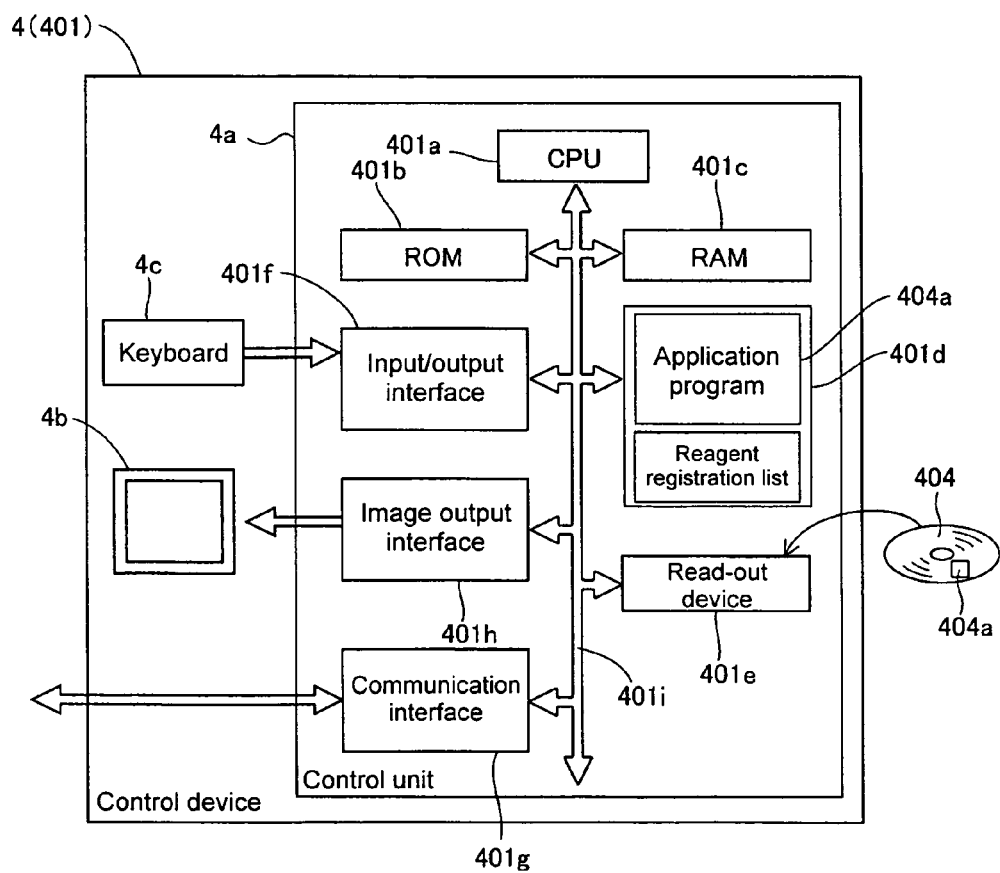
FIG. 5 is a block diagram showing a control device of the immunological analyzer according to one embodiment of the present invention.

The configuration of the control device 4 will be now described. As shown in FIG. 5, the control device 4 is configured by a computer 401 mainly comprising the control unit 4a, the display unit 4b, and the keyboard 4c. The control unit 4a is mainly configured by a CPU 401a, a ROM 401b, a RAM 401c, a hard disc 401d, a read-out device 401e, an input/output interface 401f, a communication interface 401g, and an image output interface 401h. The CPU 401a, the ROM 401b, the RAM 401c, the hard disc 401d, the read-out device 401e, the input/output interface 401f, the communication interface 401g, and the image output interface 401h are connected by a bus 401i.

The CPU 401a can execute computer programs stored in the ROM 401b and the computer programs loaded in the RAM 401c. The computer 401 serves as the control device 4 when the CPU 401a executes the application program 404a, as described below.

The ROM 401b is configured by mask ROM, PROM, EPROM, EEPROM, and the like, and is recorded with computer programs to be executed by the CPU 401a, data used for the same, and the like.

SAMPLE ANALYZER The RAM 401c is configured by SRAM, DRAM, and the like. The RAM 401c is used to read out the computer programs recorded on the ROM 401b and the hard disc 401d. The RAM 401c is used as a work region of the CPU 401a when executing the computer programs.

The hard disc 401d is installed with various computer programs to be executed by the CPU 401a such as operating system and application program, as well as data used in executing the computer program. The immunological analysis application program 404a according to the present embodiment is also installed in the hard disc 401d. The hard disc 401d is built with a database (reagent DB) related to the reagent information of the reagent installed in the reagent installing units 6 and 7, and the position information of the reagent in the reagent installing units 6 and 7. The reagent DB stores, for every reagent installed in the reagent installing units 6 and 7, position information in the reagent installing unit 6 or 7 of the reagent, measurement item, type of reagent, lot number, serial number of a reagent-containing assembly, measurable number of times at current point, expiration date, presence or absence of opponent configuring a set, and serial number of the opponent reagent configuring the set. The reagent DB is also configured to be created in time of activation of the apparatus and sequentially updated in time of measurement and replacement or retrieval of the reagent, similar to the reagent set table. The creating process and the updating process of the reagent DB will be described in detail below.

The read-out device 401e is configured by flexible disc drive, CD-ROM drive, DVD-ROM drive, and the like, and is able to read out computer programs and data recorded on a portable recording medium 404. The immunological analysis application program 404a is stored in the portable recording medium 404, wherein the computer 401 reads out the application program 404a from the portable recording medium 404, and installs the application program 404a to the hard disc 401d.

The application program 404a is not only provided by the portable recording medium 404, but also provided through communication line (wired or wireless) from external devices communicatably connected with the computer 401 through the communication line. For instance, the application program 404a may be stored in the hard disc of the server computer on the Internet, so that the computer 401 can access the server computer to download the application program 404a and install the application program 404a to the hard disc 401d.

Operating system providing graphical user interface environment such as Windows (registered trademark) manufactured and sold by US Microsoft Co. is installed in the hard disc 401d. In the following description, the application program 404a according to the first embodiment is assumed to operate on the operating system.

The input/output interface 401f is configured by serial interface such as USB, IEEE1394, RS-232C; parallel interface such as SCSI, IDE, IEEE1284; analog interface such as D/A converter, A/D converter, and the like. The keyboard 4c is connected to the input/output interface 401f, so that the user can input data to the computer 401 by using the keyboard 4c.

The communication interface 401g is, for example, Ethernet (registered trademark) interface. The computer 401 can transmit and receive data with the measurement mechanism section 2 by using a predetermined communication protocol by means of the communication interface 401g.

The image output interface 401h is connected to the display unit 4b configured by LCD, CRT, or the like, and is configured to output an image signal corresponding to the image data provided from the CPU 401a to the display unit 4b. The display unit 4b displays the image (screen) according to the input image signal. The display unit 4b is configured to display buttons for making various instructions to the apparatus, so that the apparatus performs the process corresponding to the button when the button is selected. In the display unit 4b, user can perform operations such as instruction to start or stop measurement on the apparatus, set the apparatus, instructions to replace or retrieve the reagent, and the like. The display unit 4b is configured by a touch panel, and the user can directly touch the button displayed on the display unit 4b to select the button. The button may be also selected by a pointer movable by a mouser etc. (not shown).

The immunological analysis application program 404a installed in the hard disc 401d of the control unit 4a measures the amount of antigen or antibody in the measurement sample by using the light emission amount (data of digital signal) of the measurement sample transmitted from the detector 15 of the measurement mechanism section 2.

The sample dispensing arm 5 (see FIGS. 1 and 2) has a function of dispensing the sample in the test tube 100 conveyed to the aspirating position 1a by the sample conveyance section 3 into a cuvette 150 held by a holder 11b of a rotatable table 11a of the primary reaction unit 11 to be described below. As shown in FIGS. 1 and 2, the sample dispensing arm 5 includes a motor 5a, a drive transmitting part 5b connected to the motor 5a, and an arm 5d attached to the drive transmitting part 5b by way of a shaft 5c. The drive transmitting part 5b is configured to turn the arm 5d with the shaft 5c as the center by the driving force from the motor 5a, and move the arm in the up and down direction (Z direction). A pipette 5e for aspirating and discharging the sample is arranged at the distal end of the arm 5d.

The reagent installing unit 6 (see FIGS. 1 and 2) is provided to install a reagent-containing assembly for holding a reagent container in which R1 reagent containing capture antibody is accommodated and a reagent container in which R3 reagent containing labeled antibody is accommodated. As shown in FIG. 1, the reagent installing unit 6 includes a reagent holder 20 for holding the reagent-containing assembly, a lid 30 attached to the reagent holder 20, and a raising and lowering unit 40 for replacing the reagent-containing assembly in the reagent holder 20 through a hole 30a formed in the lid 30. The raising/lowering unit 40 includes a mounting board 41 on which the reagent-containing assembly is mounted when replacing etc. the reagent-containing assembly. The lid 30 includes a hole 30b for aspirating the R1 reagent from the reagent-containing assembly held in the reagent holder 20, and a hole 30c for aspirating the R3 reagent. In the present embodiment, the reagent installing unit 6 is arranged with the barcode reader 6a for reading the barcode attached to the reagent-containing assembly.

The reagent installing unit 7 (see FIGS. 1 and 2) is arranged to install a reagent-containing assembly 300 (see FIG. 6) for holding a reagent container in which a R2 reagent containing magnetic particles is accommodated. The configuration of the reagent installing unit 7 will be described in detail below.

The reagent dispensing arm 8 (see FIGS. 1 and 2) has a function of aspirating the R1 reagent in the reagent-containing assembly installed in the reagent installing unit 6 and dispensing the aspirated R1 reagent into the cuvette 150 dispensed with the sample of the primary reaction unit 11. The reagent dispensing arm 8 includes a motor 8a, a drive transmitting part 8b connected to the motor 8a, and an arm 8d attached to the drive transmitting part 8b by way of a shaft 8c. The drive transmitting part 8b is configured to turn the arm 8d with the shaft 8c as the center by the driving force from the motor 8a, and move the arm in the up and down direction. A pipette 8e (see FIG. 1) for aspirating and discharging the R1 reagent in the reagent-containing assembly is arranged at the distal end of the arm 8d. That is, the pipette 8e is configured to aspirate the R1 reagent in the reagent-containing assembly installed in the reagent installing unit 6, and thereafter, dispense the aspirating R1 reagent into the cuvette 150 dispensed with the sample of the primary reaction unit 11.

The reagent dispensing arm 9 (see FIGS. 1 and 2) has a function of dispensing the R2 reagent in the reagent-containing assembly 300 installed in the reagent installing unit 7 into the cuvette 150 dispensed with the sample and the R1 reagent of the primary reaction unit 11. The reagent dispensing arm 9 includes a motor 9a, a drive transmitting part 9b connected to the motor 9a, and an arm 9d attached to the drive transmitting part 9b by way of a shaft 9c. The drive transmitting part 9b is configured to turn the arm 9d with the shaft 9c as the center by the driving force from the motor 9a, and move the arm in the up and down direction. A pipette 9e (see FIG. 1) for aspirating and discharging the R2 reagent in the reagent-containing assembly 300 is arranged at the distal end of the arm 9d. Thus, the pipette 9e is configured to aspirate the R2 reagent in the reagent-containing assembly 300 installed in the reagent installing unit 7, and thereafter, dispense the aspirated R2 reagent into the cuvette 150 dispensed with the sample and the R1 reagent of the primary reaction unit 11.

The reagent dispensing arm 10 (see FIGS. 1 and 2) has a function of aspirating the R3 reagent in the reagent-containing assembly installed in the reagent installing unit 6, and dispensing the aspirated R3 reagent into the cuvette 150 dispensed with the sample, the R1 reagent, and the R2 reagent of the secondary reaction unit 12. The reagent dispensing arm 10 includes a motor 10a, a drive transmitting part 10b connected to the motor 10a, and an arm 10d attached to the drive transmitting part 10b by way of a shaft 10c. The drive transmitting part 10b is configured to turn the arm 10d with the shaft 10c as the center by the driving force from the motor 10a, and move the arm in the up and down direction. A pipette 10e (see FIG. 1) for aspirating and discharging the R3 reagent in the reagent-containing assembly installed at the reagent installing unit 6 is arranged at the distal end of the arm 10d. That is, the pipette 10e is configured to aspirate the R3 reagent in the reagent-containing assembly installed in the reagent installing unit 6, and thereafter, dispense the aspirated R3 reagent into the cuvette 150 dispensed with the sample, the R1 reagent, and the R2 reagent of the secondary reaction unit 12.

As shown in FIGS. 1 and 2, the primary reaction unit 11 is arranged to rotatably transfer the cuvette 150 held by the holder 11b of the rotatable table 11a by a predetermined angle for every predetermined period (18 seconds in the present embodiment), and to stir the sample, the R1 reagent, the and the R2 reagent in the cuvette 150. That is, the primary reaction unit 11 is arranged to react the R2 reagent containing magnetic particles and the antigen in the sample in the cuvette 150. The primary reaction unit 11 is configured by a rotatable table 11a for conveying the cuvette 150 accommodating the sample, the R1 reagent, and the R2 reagent in the rotating direction, and a container conveying part 11c for stirring the sample, R1 reagent, and R2 reagent in the cuvette 150 and conveying the cuvette 150 accommodating the stirred sample, R1 reagent and R2 reagent to the BF separator 14 (see FIGS. 1 and 2) to be described below.

The rotatable table 11a is configured so as to rotatably transfer the cuvette 150 held in the holder 11b by a predetermined angle for every 18 seconds. Thus, various devices (sample dispensing arm 5, reagent dispensing arms 8 and 9 etc.) of the immunological analyzer 1 are controlled so as to operate on the cuvette 150 at the predetermined transferred position at a timing that the cuvette is transferred to the predetermined position by the rotatable table 11a.

The container conveying part 11c is rotatably arranged at the central portion of the rotatable table 11a. The container conveying part 11c has a function of gripping the cuvette 150 held in the holder 11b of the rotatable table 11a and stirring the sample in the cuvette 150. Furthermore, the container conveying part 11c has a function of conveying the cuvette 150 accommodating the sample obtained by stirring and incubating the sample, the R1 reagent and the R2 reagent to the BF separator 14 (see FIGS. 1 and 2).

The secondary reaction unit 12 (see FIGS. 1 and 2) has a configuration similar to the primary reaction unit 11, and is arranged to rotatably transfer the cuvette 150 held by the holder 12b of the rotatable table 12a by a predetermined angle for every predetermined period (18 seconds in the present embodiment), and to stir the sample, the R1 reagent, the R2 reagent, the R3 reagent, and the R5 reagent in the cuvette 150. That is, the secondary reaction unit 12 is arranged to react the R3 reagent containing labeled antibody and the antigen in the sample in the cuvette 150, and to react the R5 reagent containing light emitting substrates and the labeled antibody of the R3 reagent. The R5 reagent is dispensed into the cuvette 150 accommodating the sample, the R1 reagent, the R2 reagent, and the R3 reagent of the secondary reaction unit 12 by a R5 reagent dispensing arm (not shown) arranged near the secondary reaction unit 12. The secondary reaction unit 12 is configured by the rotatable table 12a for conveying the cuvette 150 accommodating the sample, the R1 reagent, the R2 reagent, the R3 reagent, and the R5 reagent in the rotating direction, and a container conveying part 12c for stirring the sample, the R1 reagent, the R2 reagent, R3 reagent, and the R5 reagent in the cuvette 150 and conveying the cuvette 150 accommodating the stirred sample etc. to the BF separator 14. The container conveying part 12c has a function of again conveying the cuvette 150 processed by the BF separator 14 to the holder 12b of the rotatable table 12. The detailed structure of the secondary reaction unit 12 is similar to the primary reaction unit 11, and thus the description thereof will be omitted.

The cuvette supplying unit 13 (see FIGS. 1 and 2) is configured to sequentially supply a plurality of cuvettes 150 to the holder 11b of the rotatable table 11a of the primary reaction unit 11.

The BF separator 14 has a function of separating the non-reacting R1 reagent (unnecessary component) and the magnetic particles from the sample in the cuvette 150 conveyed by the container conveying part 11c of the primary reaction unit 11, and a function of separating the non-reacting R3 reagent (unnecessary component) and the magnetic particles from the sample in the cuvette 150 (see FIG. 1) conveyed by the container conveying part 12c of the secondary reaction unit 12.

The detector 15 (see FIGS. 1 and 2) is arranged to measure the amount of antigen contained in a sample by acquiring the light generated in the reaction process of the labeled antibody bound to the antigen of the sample performed with a predetermined process and the light emitting substrate with a photo multiplier tube.

Figure 6:
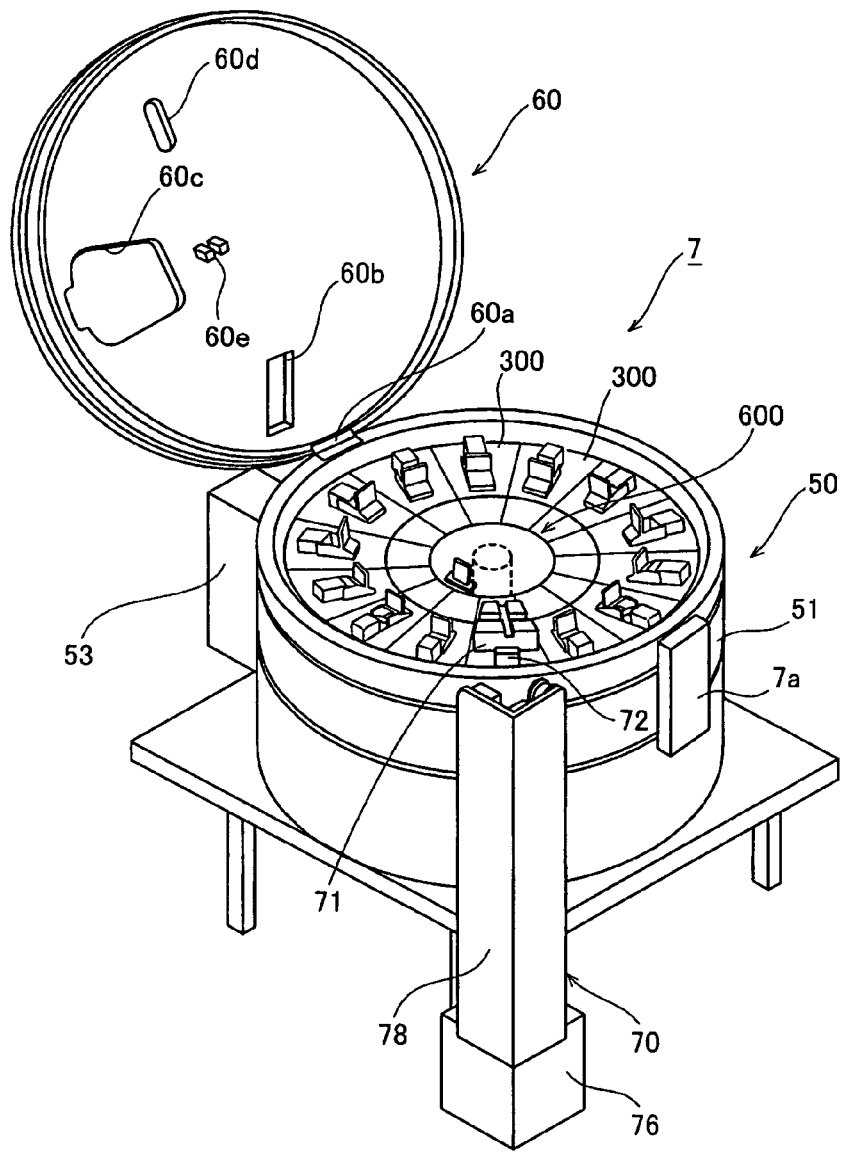
FIG. 6 is a perspective view showing an overall configuration of a reagent installing unit shown in FIG. 1.
Figure 10:
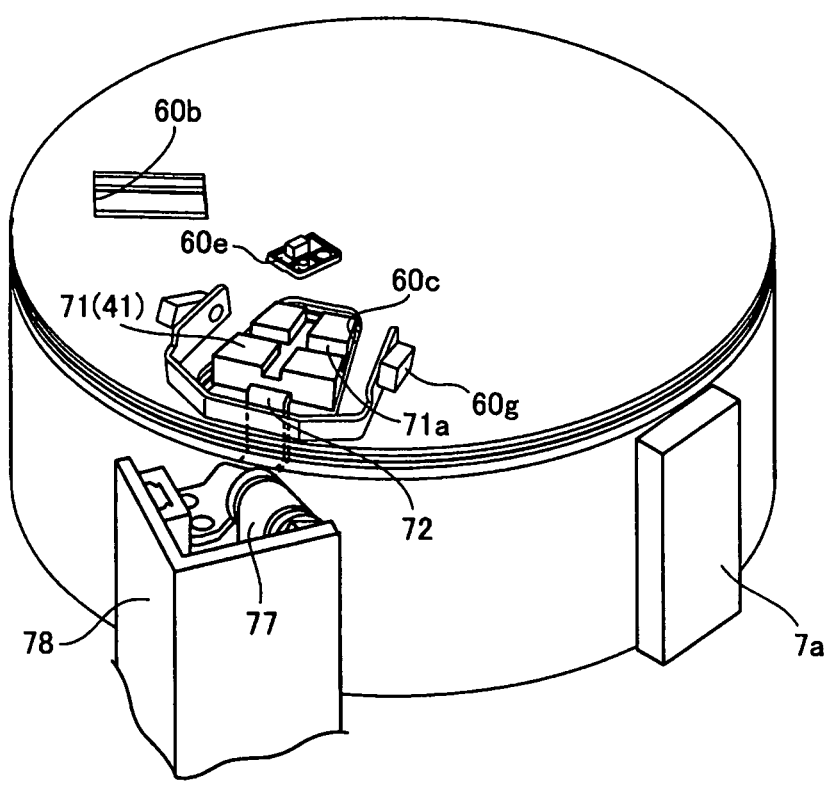
FIG. 10 is a perspective view showing a reagent installing unit shown in FIG. 6.
Figure 11:
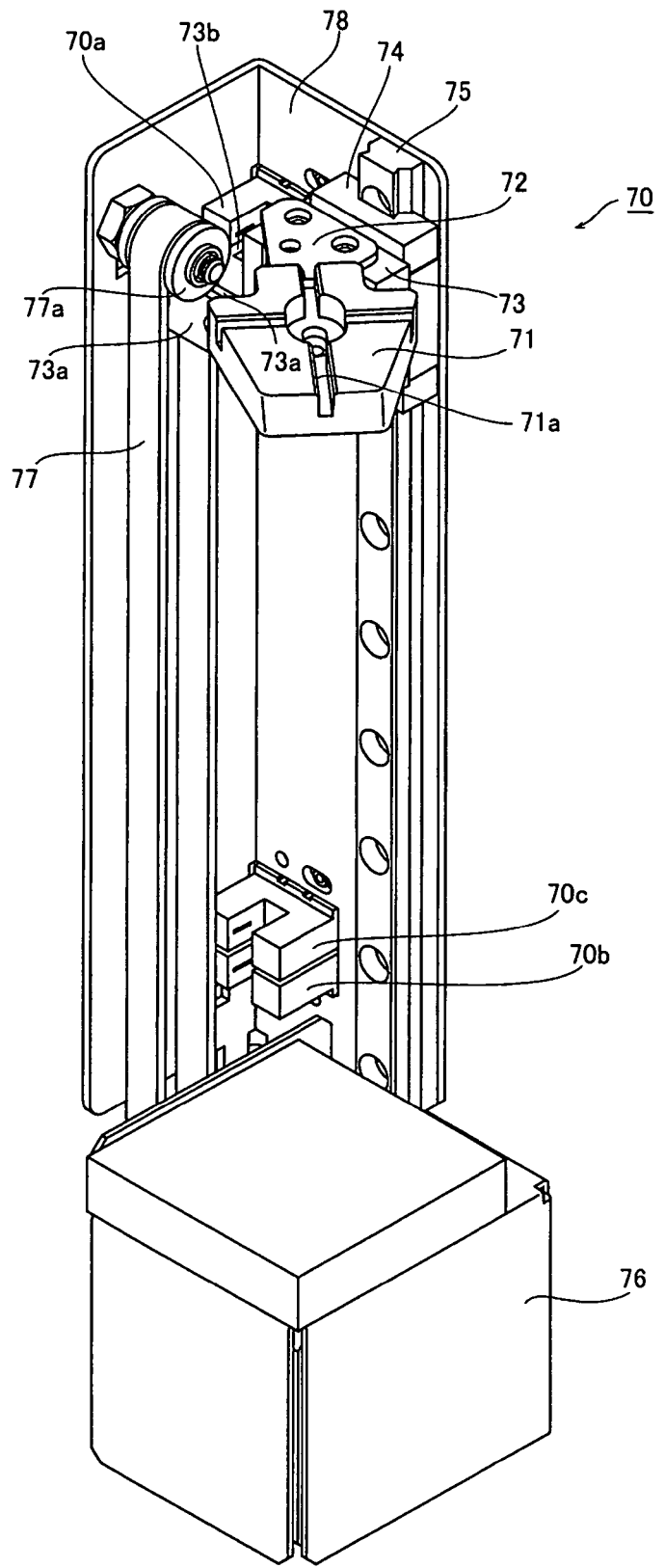
FIG. 11 is a perspective view showing a raising/lowering unit according to one embodiment.
Figure 12:
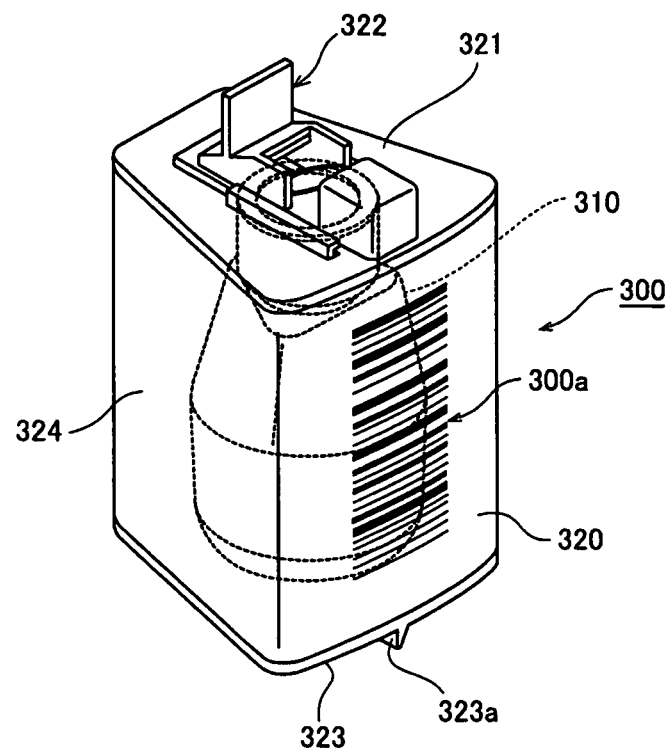
FIG. 12 is a perspective view showing a reagent-containing assembly accommodating R2 reagent.
Figure 13:
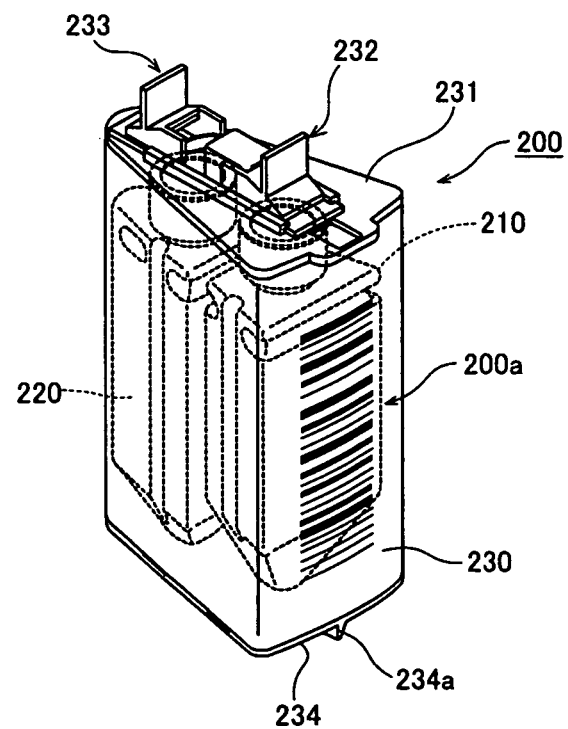
FIG. 13 is a perspective view showing a reagent-containing assembly accommodating R1/R3 reagent.

FIGS. 7 to 11 are views describing details of the reagent installing unit shown in FIG. 6. FIGS. 12 and 13 are perspective views showing the reagent-containing assembly accommodating the R2 reagent and the reagent-containing assembly accommodating the R1/R3 reagent, respectively. The structures of the reagent installing unit 7 of the immunological analyzer 1 according to one embodiment of the present invention, the reagent-containing assembly 300 installed in the reagent installing unit 7, and the reagent-containing assembly 200 installed in the reagent installing unit 6 will be described with references to FIGS. 1, 2 and 6 to 13.

As shown in FIG. 6, the reagent installing unit 7 includes a cylindrical reagent holder 50 for holding the reagent-containing assembly 300 in a circular ring shape, a lid 60 attached to the reagent holder 50 in an openable and closable manner, and a raising/lowering unit 70 attached to the side surface (outer wall part 51) of the cylindrical reagent holder 50. The barcode reader 7a for reading the barcode 300a (see FIG. 12) attached to the reagent-containing assembly 300 installed in the reagent installing unit 7 is arranged at the side surface (outer wall part 51) of the reagent installing unit 7. A Peltier element (not shown) is also attached at the bottom of the reagent installing unit 7, and the inside of the reagent installing unit 7 is maintained at about 15° C.

Figure 7:
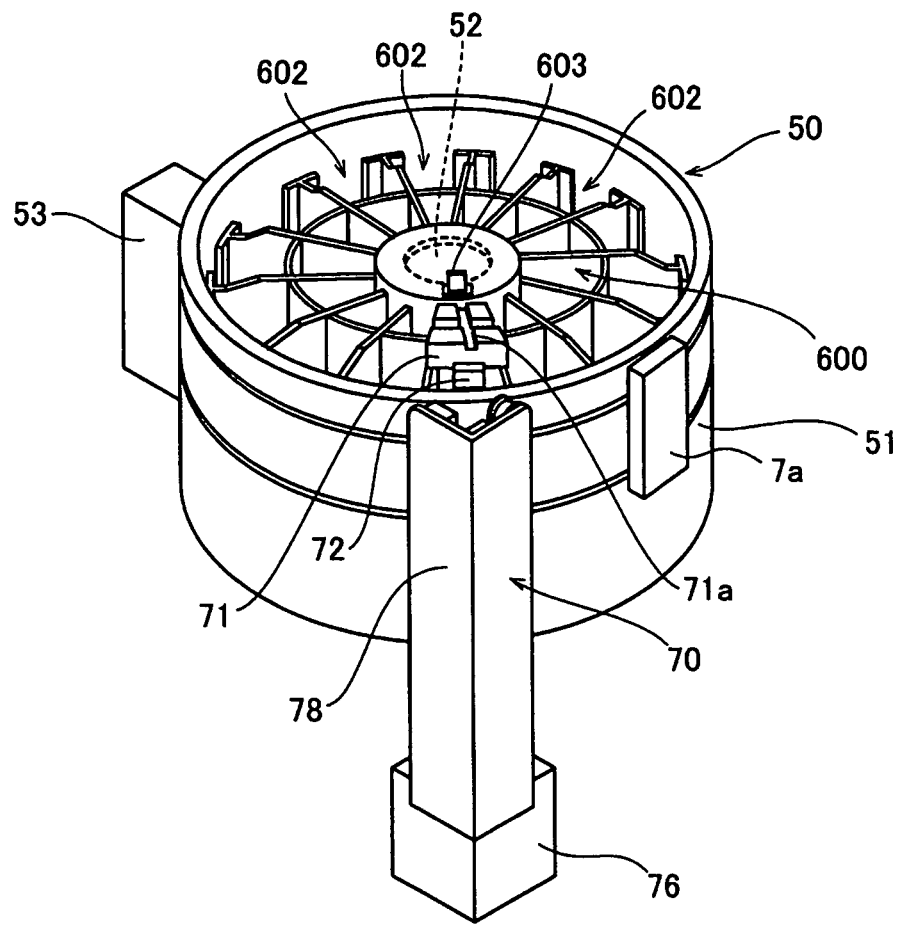
FIG. 7 is a perspective view showing a reagent holder of the reagent installing unit shown in FIG. 6.
Figure 8:
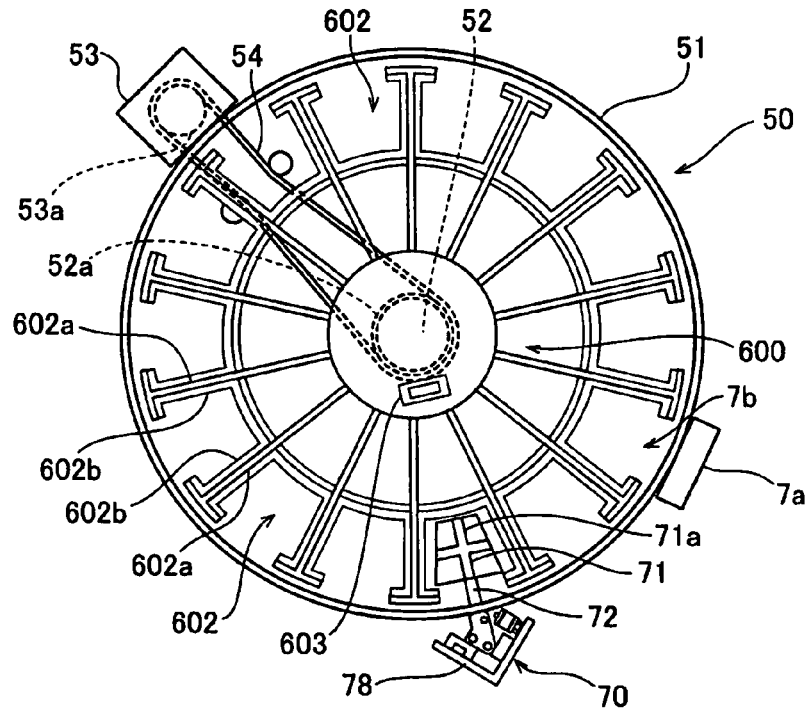
FIG. 8 is a plan view of the reagent holder of the reagent installing unit shown in FIG. 7.

As shown in FIGS. 7 and 8, the reagent holder 50 includes a cylindrical outer wall part 51, a rotatable rotation shaft 52 arranged at the center, a stepping motor 53 for rotating the rotation shaft 52, and a belt 54 for transmitting the driving force of the stepping motor 53 to the rotation shaft 52 (see FIG. 8). A heat insulating material (not shown) is attached over the entire surface on the inner surface of the outer wall part 51, so that the temperature inside the reagent holder 50 is maintained at low temperature (about 15° C.). As shown in FIG. 8, the driving force of the stepping motor 53 is transmitted to the rotation shaft 52 via the belt 54 by a pulley 53a rotated by the stepping motor 53 and a pulley 52a coaxially fixed to the rotation shaft 52.

Figure 9:
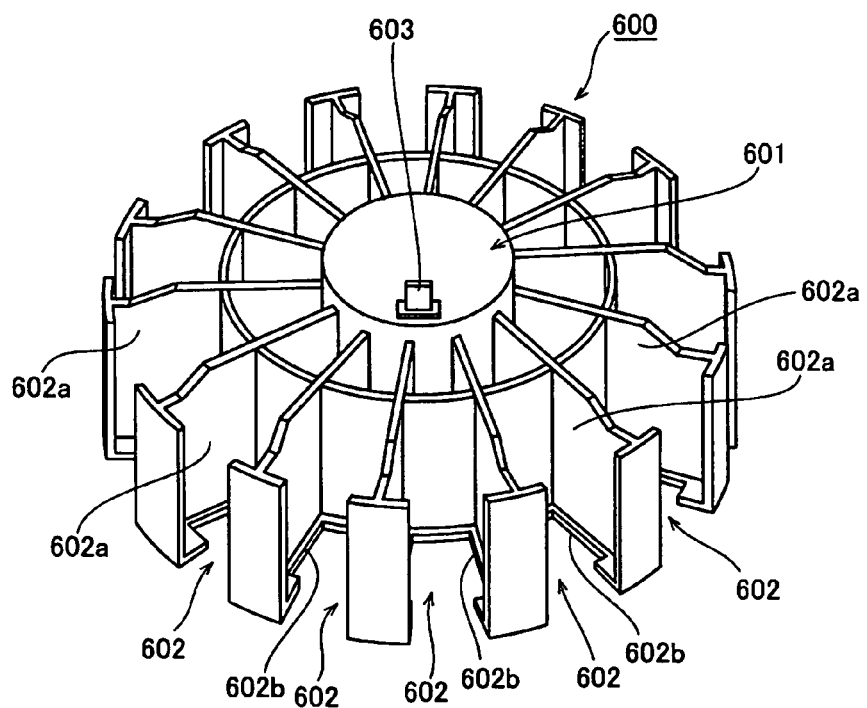
FIG. 9 is a perspective view showing a rack for holding the reagent-containing assembly used in the immunological analyzer according to one embodiment of the present invention.

A rack 600 for holding a plurality of reagent-containing assemblies 300 in a circular ring form is fixedly attached to the rotation shaft 52. The rack 600 holding the reagent-containing assemblies 300 rotates when the rotation shaft 52 is rotated with the reagent-containing assemblies 300 held in the rack 600, and thus the reagent-containing assembly 300 holding the reagent to be aspirated can be moved to below a hole 60b and an input/output hole 60c of the lid 60 to be described below. As shown in FIG. 9, the rack 600 includes an inserting part 601, formed at the center of the rack 600, to which the rotation shaft 52 is inserted; a plurality of holders 602, formed in a circular ring form with the inserting part 601 as the center, for holding the reagent-containing assembly 300; and an origin detection strip 603 arranged so as to project above the inserting part 601. The holder 602 is configured by a partition plate 602a and a supporting part 602b. The partition plate 602a is arranged in plurals at a predetermined angular interval so as to radially extend from the inserting part 601. The supporting part 602b is arranged at the lower part of the portions facing each other of the partition plates 602a and at the lower part of the inserting part 601 so as to project to the inner side. Each reagent-containing assembly 300 is arranged so that a peripheral edge of a bottom part 323 (see FIG. 12) is supported by a supporting part 602b in a space sandwiched by a pair of partition plates 602a. A mounting board 71 and the arm 72 of the raising/lowering unit 70 for raising and lowering the reagent-containing assembly 300 is configured to be raised and lowered without contacting the holder 602 of the rack 600 by having an upper part, a lower part, and an outside part in the radial direction of the holder 602 as open ends.

As shown in FIG. 6, the lid 60 is attached in an openable and closable manner to the reagent holder 50 by way of a hinge part 60a. The lid 60 is configured to shield outside air so that the temperature inside the reagent installing unit 7 is maintained at a low temperature (15° C.), and so as to enable the reagent in the reagent installing unit 7 to be aspirated from the outside and the reagent-containing assembly 300 to be placed in or taken out from the reagent installing unit 7. Specifically, the lid 60 includes the hole 60b to be inserted with a pipette 9e of the reagent dispensing arm 9 when aspirating the reagent from the reagent container 310 (FIG. 12) of the reagent-containing assembly 300, and the input/output hole 60c for placing in or taking out the reagent-containing assembly 300 from the reagent installing unit 7 by the raising/lowering unit 70. The lid 60 is arranged with a reflection sensor 60d for detecting whether or not the reagent-containing assembly 300 is held in the holder 602 of the rack 600, a transmissive origin detection sensor 60e for detecting an origin position of the rack 600, and a transmissive sensor 60g (see FIG. 10) for detecting the reagent-containing assembly 300 mounted on the mounting board 71 of the raising/lowering unit 70 to be described below. The origin point detection sensor 60e is arranged on the back surface side of the lid 60, and the sensor 60f is arranged on the front surface side of the lid 60. The sensor 60g is arranged on the front surface side of the lid 60 so as to cross the input/output hole 60c. The transmissive origin detection sensor 60e has a function of detecting an origin detection strip 603 arranged on the rack 600 and detecting the origin position of the rotating rack 600.

In the present embodiment, the raising/lowering unit 70 is arranged to place in and take out the reagent-containing assembly 300 into/from the reagent installing unit 7. As shown in FIG. 11, the raising/lowering unit 70 includes the mounting board 71 to be mounted with the reagent-containing assembly 300, an arm 72 for supporting the mounting board 71, a supporting member 73 for supporting the arm 72, a linear movement guide including a slider 74 to be fixed with the supporting member 73 and a guide rail 75 for slidably supporting the slider 74 in the up and down direction, a motor 76, a belt 77 for transmitting the driving force of the motor 76, and a bracket 78. Three transmissive sensors 70a, 70b, and 70c are attached to the bracket 78.

The mounting board 71 has a function of holding the reagent-containing assembly 300 at the holder 602 of the rack 600 by being lowered with the reagent-containing assembly 300. The mounting board 71 is raised from the lower side of the holder 602 for holding the reagent-containing assembly 300 to lift the reagent-containing assembly 300 of the holder 602 and retrieve it from the input/output hole 60c of the lid 60. A cross-shaped groove 71a capable of engaging the rib 323a arranged at the bottom 323 of the reagent-containing assembly 300 is formed in the mounting board 71.

As shown in FIG. 11, two-way fixed strip 73a formed on the supporting member 73 is fixed to be belt 77 with the belt 77 sandwiched in between. The driving force of the motor 76 is transmitted to the supporting member 73 by way of the belt 77. A detection strip 73b is arranged on the supporting member 73 in a projecting manner. The detection strip 73b is detected by the sensors 70a, 70b, and 70c, so that the position in the up and down direction of the mounting board 71 is detected. Specifically, when the detection strip 73b is detected by the sensor 70a, the mounting board 71 is positioned at a mounting/retrieving position (top dead point) capable of being mounting/retrieving the reagent-containing assembly 300. When the detection strip 73b is detected by the sensor 70b, the mounting board 71 is positioned on the lower side (bottom dead point) of the holder 602 of the rack 600. The mounting board 71 is arranged on the lower side of the reagent-containing assembly 300 held in the rack 600 when positioned at the bottom dead point, whereby the rack 600 can be rotated. A predetermined clearance region is formed between the rack 600 and the bottom dead point, and the sensor 70c detects the detection strip 73b. The control unit 2a recognizes that the mounting board 71 is positioned in the clearance region between the holder 602 of the rack 600 and the bottom dead point. When the mounting board 71 is positioned in the clearance region, contact between the mounting board 71 and the rack 600 is avoided by rotating the rack 600. The belt 77 is configured to be rotation driven the pulley (not shown) arranged coaxially with the rotation shaft (not shown) of the motor 76, and pulley 77a arranged on the upper side.

The barcode reader 7a is configured to read the barcode 300a (see FIG. 12) of the reagent-containing assembly 300 positioned at the barcode reading position 7b (see FIG. 8).

As shown in FIG. 12, the reagent-containing assembly 300 includes a reagent container 310 containing the R2 reagent including magnetic particles and a case 320 for accommodating the reagent container 310. A slide lid 322 for sealing the reagent container 310 is arranged on the upper surface 321 of the case 320. The slide lid 322 is opened/closed by a slide lid open/close mechanism (not shown) arranged on the lid 60. A rib 323a that engages the groove 71a of the mounting board 71 of the raising/lowering unit 70 is arranged at the bottom surface 323 of the case 320. The barcode 300a is attached to the side surface of the reagent-containing assembly 300. The barcode 300a contains reagent information related to the R2 reagent contained in the reagent container 310 of the reagent-containing assembly 300. Specifically, the reagent information includes measurement item, type of reagent, lot number, serial number of reagent-containing assembly 300, initial measurable number of times, and expiration data of the reagent.

As shown in FIG. 13, the reagent-containing assembly 200 includes a reagent container 210 accommodating the R1 reagent, a reagent container 220 accommodating the R3 reagent, and a case 230 for accommodating the reagent containers 210 and 220. Slide lids 232 and 233 for sealing the reagent containers 210 and 220 are arranged on the upper surface 231 of the case 230. A rib 234a that engages a groove 41a (see FIGS. 1 and 2) of the mounting board 41 of the raising/lowering unit 40 is arranged at the bottom surface 234 of the case 230. Similar to the reagent-containing assembly 300, the barcode 200a containing reagent information related to the reagent (R1 reagent and R3 reagent) contained in the reagent-containing assembly 200 is attached to the side surface of the reagent-containing assembly 200.

The reagent installing unit 6 has a configuration similar to the reagent installing unit 7 except that two slide lid open/close mechanisms (not shown) are arranged on the lid 30 in correspondence to the reagent-containing assembly 200 including two reagent containers of R1 reagent and R2 reagent, and thus the detailed description thereof will be omitted.

In the present embodiment, the magnetic particles are heavy and tend to easily sediment, and thus the R2 reagent in the reagent-containing assembly 300 is stirred by rotating in a reciprocating manner the rack 600 holding the reagent-containing assembly 300 in the reagent installing unit 7 accommodating the R2 reagent. In the reagent installing unit 6, the R1 reagent and the R3 reagent do not need to be stirred, and thus stirring of reagent by rotating the rack in a reciprocating manner is not performed as opposed to the reagent installing unit 7. One measurement item is measured by using a plurality of R1 reagent and R3 reagent installed in the reagent installing unit 6 and the R2 reagent installed in the reagent installing unit 7. In the immunological analyzer 1 according to the present embodiment, the reagent-containing assembly 200 containing the R1 reagent and the R3 reagent to be used in the measurement of one measurement item and the reagent-containing assembly 300 containing the R2 reagent used in the measurement item same as the relevant measurement item are set and recognized based on the reagent information by the barcodes 200a and 300a. Specifically, when the measurement item and the lot number of the reagent contained in the reagent-containing assembly 200 and the measurement item and the lot number of the reagent contained in the reagent-containing assembly 300 match, the immunological analyzer 1 sets such reagents and recognizes the same. In the immunological analyzer 1, management of the reagent such as replacement in units of sets of R1 reagent, R2 reagent, and R3 reagent can be performed. The management of the reagent will be described in detail below.

FIGS. 14 to 18 are views showing a screen displayed on the display unit of the control device. The configuration of the screen displayed on the display unit will be described with reference to FIGS. 14 to 18.

Figure 14:
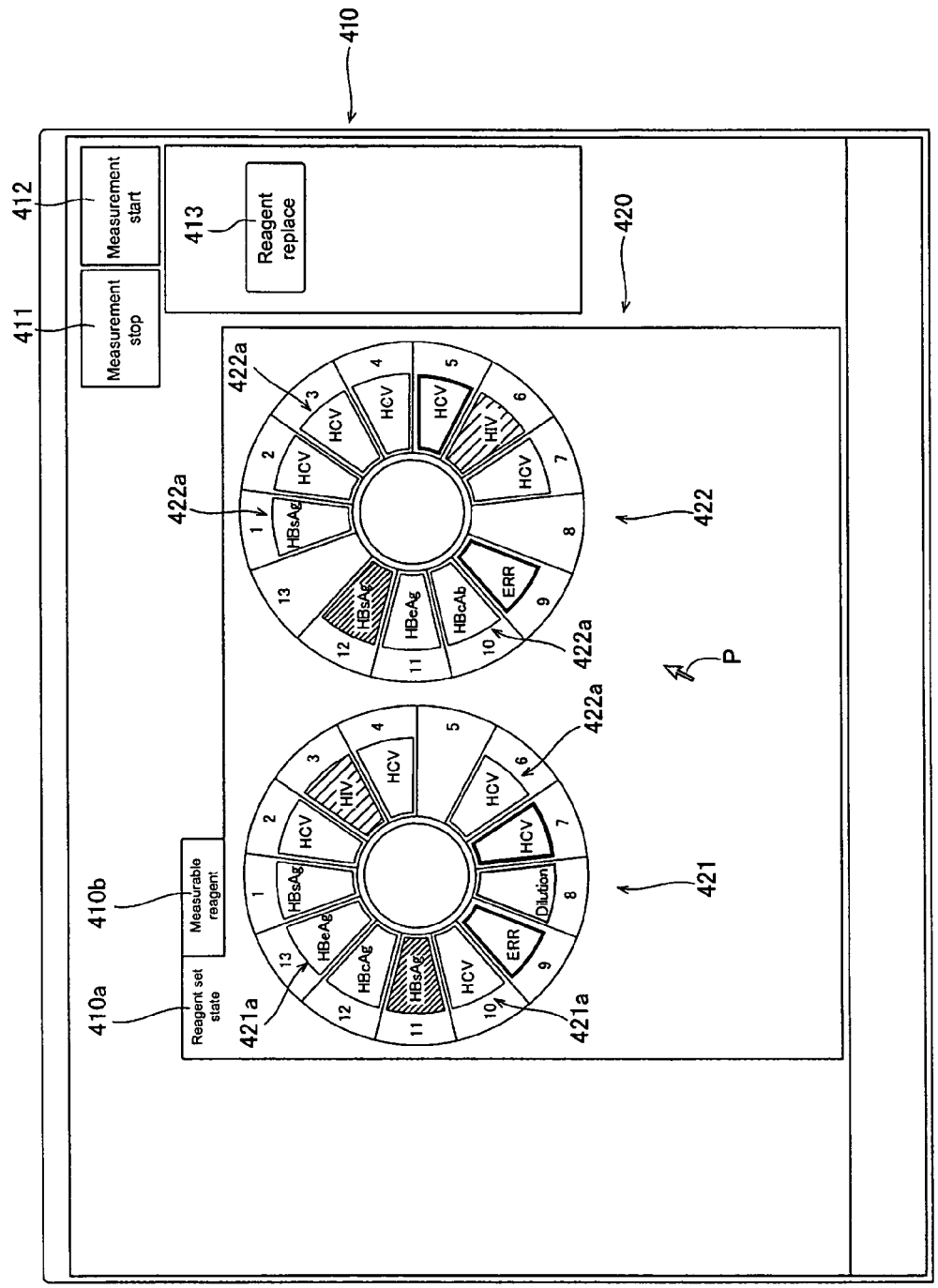
FIG. 14 is a view showing a reagent arrangement state screen of a reagent management screen.

In the present embodiment, the control device 4 is configured to display a reagent management screen 410 for managing the reagent on the display unit 4b, as shown in FIG. 14. In the reagent management screen 410, a reagent arrangement state screen 420 showing the arrangement state of the reagent-containing assembly 200 (R1 reagent and R3 reagent) in the reagent installing unit 6 and the arrangement state of the reagent-containing assembly 300 (R2 reagent) in the reagent installing unit 7 is displayed by selecting a tab (reagent set state) 410a.

The reagent arrangement state screen 420 includes a reagent arrangement display region 421 corresponding to the reagent installing unit 6 and a reagent arrangement display region 422 corresponding to the reagent installing unit 7. The reagent arrangement display region 421 displays a mark 421a showing the reagent-containing assembly 200 held at each position in a circular ring form in correspondence to the arrangement state of the reagent-containing assembly 200 actually arranged in the reagent installing unit 6. Numbers from 1 to N (N=13 in the present embodiment) showing the position information in the reagent installing unit 6 is assigned in correspondence to each mark 421a. The measurement item of the reagent (R1 reagent and R3 reagent) contained in the reagent-containing assembly 200 is displayed in the mark 421a. Similar to the reagent arrangement display region 421, a mark 422a containing the measurement item of the reagent (R2 reagent) contained in the reagent-containing assembly 300 is displayed in a circular ring form in correspondence to the reagent installing unit 7 in the reagent arrangement display region 422.

In the reagent arrangement state screen 420, the reagent contained in the reagent-containing assembly 200 and the reagent contained in the reagent-containing assembly 300 are recognized by the apparatus as a set, if determined to be usable for the measurement (if there is no problem in measurement), the marks 421a and 422a corresponding to the respective reagent-containing assembly are displayed with a predetermined color (white in the present embodiment). In FIG. 14, for instance, the mark 422a (hereinafter referred to as reagent "1") of the position information "1" (measurement item "HBsAg") in the reagent arrangement display region 422 is displayed in white, indicating that the reagent-containing assembly 200 forming a set with the reagent-containing assembly 300 corresponding to the reagent "1" is installed in the reagent installing unit 6. Similarly, indication is made that the reagent-containing assembly 200 forming a set is installed in the reagent installing unit 6 with respect to reagent "2" to reagent "4", reagent "7", reagent "10" and reagent "11" of the reagent arrangement display region 422.

In the reagent arrangement state screen 420, if there is no problem in the reagent itself but a warning is necessary (if a standard curve necessary for outputting the final analysis result has not been prepared, and if remaining quantity (measurable number of times) is less than ten times), the marks 421a and 422a corresponding to the respective reagent-containing assembly are displayed in a predetermined color (yellow in the present embodiment, diagonal lines of wide interval in the figure). For instance, reagent "6" (measurement item "HIV") of the reagent arrangement display region 422 and reagent "3" (measurement item "HIV") of the reagent arrangement display region 421 are displayed in yellow, indicating that either the standard curve has not been prepared or the remaining quantity (measurable number of times) is less than ten times.

In the reagent arrangement state screen 420, if there is a problem in the reagent itself (if remaining quantity (measurable number of times) of the reagent is zero and if expiration date is expired), the marks 421a and 422a corresponding to the respective reagent-containing assembly are displayed in a predetermined color (red in the present embodiment, diagonal lines of narrow interval in the figure). For instance, reagent "12" (measurement item "HBsAg") of the reagent arrangement display region 422 and reagent "11" (measurement item "HBsAg") of the reagent arrangement display region 421 are displayed in red, indicating that either the remaining quantity (number of measurable times) of the reagent is zero or the expiration date is expired.

In the reagent arrangement state screen 420, if the reading of the barcode (barcodes 200a and 300a) fails, the marks 421a and 422a corresponding to the respective reagent-containing assembly have the peripheral edge displayed in a predetermined color (red in the present embodiment, peripheral edge of the mark shown with heavy line in the figure), and the display in the mark shows "ERR" instead of the measurement item. For instance, reagent "9" of the reagent arrangement display region 422 and reagent "9" of the reagent arrangement display region 421 have the peripheral edge displayed in red and the display in the mark as "ERR", indicating that the reading of the barcode attached to the reagent-containing assembly fails and the reagent information is not recognized by the apparatus.

In the reagent arrangement state screen 420, if the reagent forming a set with the reagent of the reagent-containing assembly installed in one reagent installing unit does not exist in the other reagent installing unit, the marks 421a and 422a corresponding to the reagent-containing assembly installed in one reagent installing unit have the peripheral edge displayed in a predetermined color (red in the present embodiment). For instance, reagent "5" (measurement item "HCV") of the reagent arrangement display region 422 and reagent "7" (measurement item "HCV") of the reagent arrangement display region 421 have the peripheral edge displayed in red, indicating that the reagent (reagent which measurement item and lot number match) forming a set with such reagent does not exist. Therefore, the mark (only the peripheral edge is red) in the case of the reagent forming the set does not exist is displayed so as to be distinguished from the mark (white, yellow, red, or red peripheral edge and display of the mark as "ERR") in the case of the reagent forming the set exists.

Figure 15:
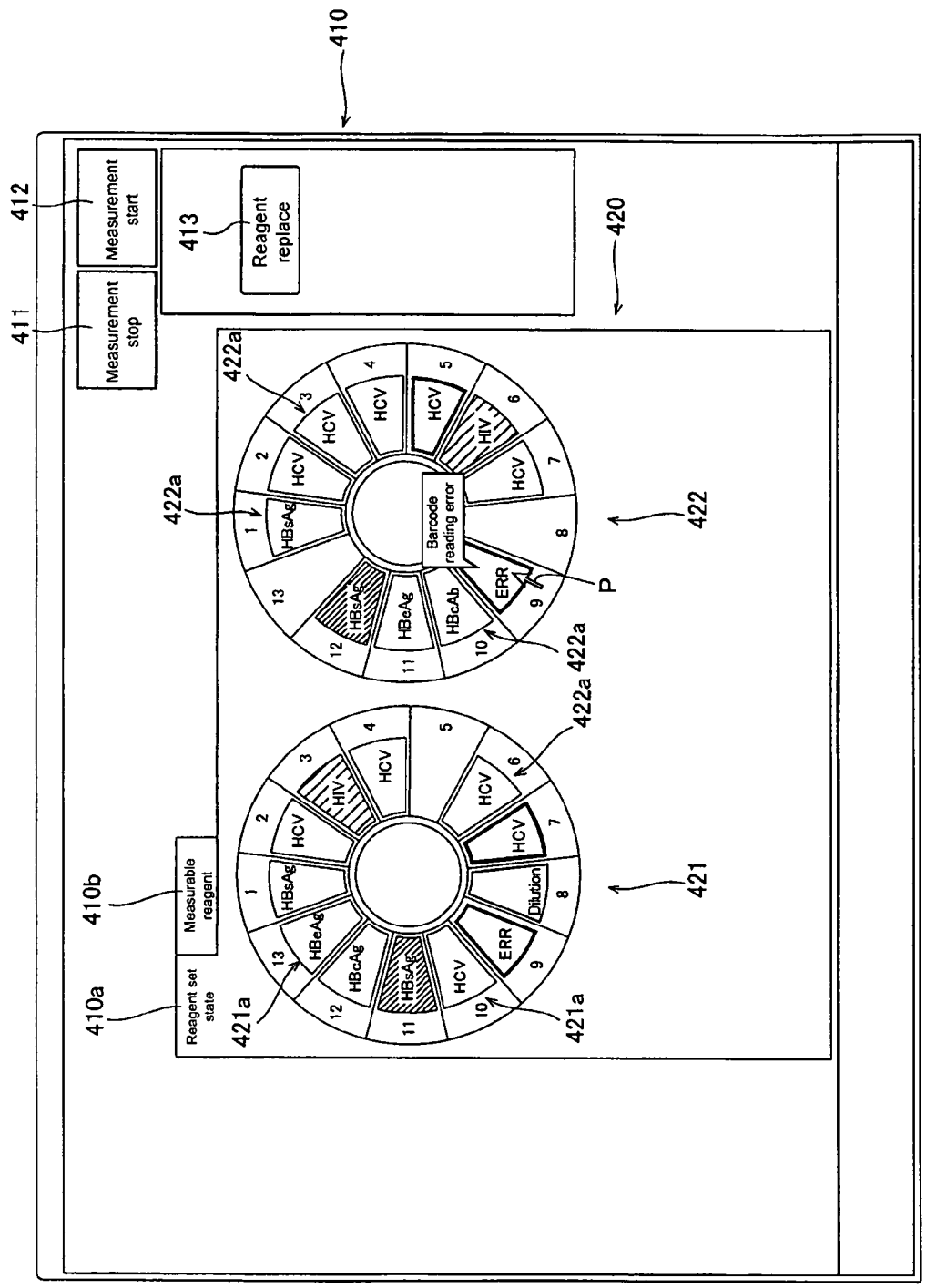
FIG. 15 is a view showing a reagent arrangement state screen of a reagent management screen.

As shown in FIG. 15, the display explaining the state of the reagent corresponding to the selected mark is displayed by selecting the mark 421a or 422a with the pointer P. For instance, if reagent "9" of the reagent arrangement display region 422 is selected, "barcode reading error" is displayed. If reagent "12" of the reagent arrangement display region 422 is selected, "measurable number of times is zero" is displayed.

Figure 16:
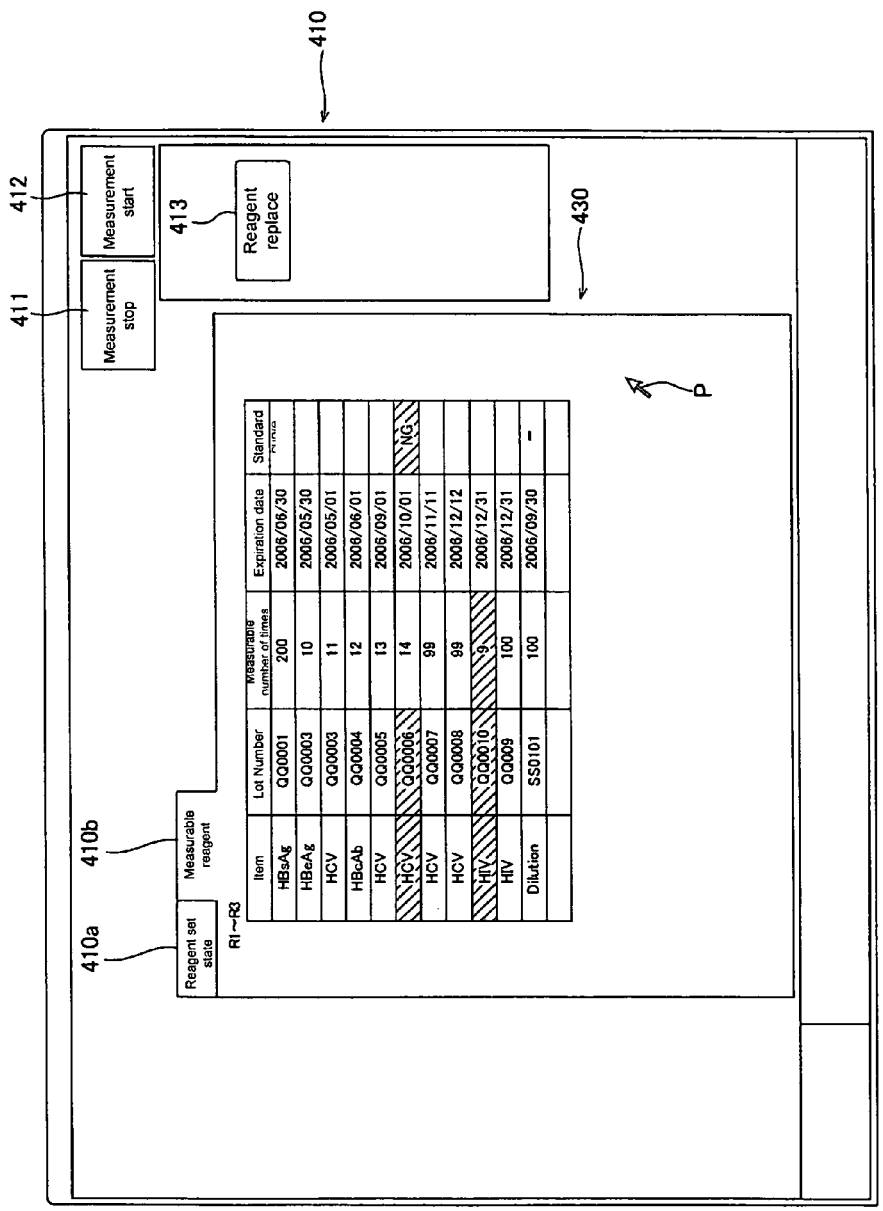
FIG. 16 is a view showing a measurable item screen of the reagent management screen.

In the present embodiment, the control device 4 is configured to display a measurable item screen 430 showing the measurable measurement items on the display unit 4b, as shown in FIG. 16. The measurable item screen 430 is displayed by selecting a tab (measurable reagent) 410b.

The measurable measurement items in which a set is formed when the measurement item and the lot number of the reagent (R1 reagent and R3 reagent) of the reagent-containing assembly 200 and the reagent (R2 reagent) of the reagent-containing assembly match is displayed on the measurable item screen 430. The user can check the measurable measurement items at the current time by referencing the measurable item screen 420. If the standard curve has not been prepared and if the remaining quantity (number of measurable times) is less than ten times in the measurable item screen 420, the portions corresponding to such measurement items are displayed in a predetermined color (yellow in the present embodiment, diagonal lines in the figure). For instance, in the measurement item which measurement item is "HCV" and the lot number is "QQ0006", the portions of the item, the lot number, and the standard curve are displayed in yellow since the standard curve has not been prepared. In the measurement item which measurement item is "HCV" and the lot number is "QQ0010", the portions of the item, the lot number, and the number of measurable times are displayed in yellow since the number of measurable times is nine times (less than ten times).

Figure 17:
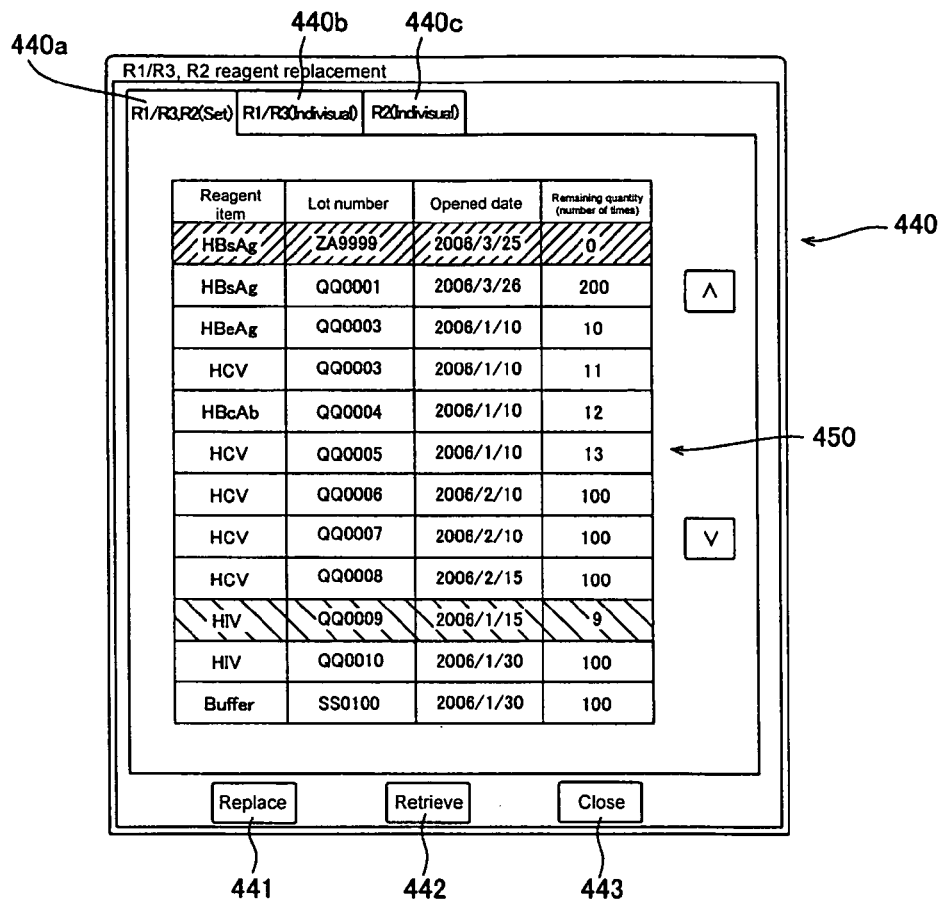
FIG. 17 is a view showing a reagent replacement screen.

The reagent management screen 410 includes a measurement start button 411 for instructing the apparatus to start the measurement, a measurement stop button 412 for instructing the apparatus to stop the measurement, and a reagent replacement button 413 for instructing the apparatus to replace the reagent. As shown in FIG. 17, the control device 4 is configured to display a reagent replacement screen 440 when the reagent replacement button 413 is selected by the user.

The reagent replacement screen 440 includes a set reagent replacement screen 450 for replacing the reagents forming a set of combination all at once, an individual reagent replacement screen (not shown) for replacing only the reagent of the reagent installing unit 6, and an individual reagent replacement screen (not shown) for replacing only the reagent of the reagent installing unit 7. The set reagent replacement screen 450 is configured to be displayed when the tab (R1/R3, R2 (set) 440a is selected. The individual reagent replacement screen (not shown) for replacing only the reagent of the reagent installing unit 6 and the individual reagent replacement screen (not shown) for replacing only the reagent of the reagent installing unit 7 are respectively configured to be displayed by selecting the tab (R1/R3 (individual)) 440b and the tab (R2 (individual)) 440c. The reagent replacement screen 440 includes a replacement button 441, a retrieval button 442, and a cancel button 443.

The set reagent replacement screen 450 is displayed with the reagent forming a set of combination, or the set of reagents that can be replaced or retrieved. The set reagent replacement screen 450 is configured to display the state of the set of reagents by colors, similar to the reagent arrangement state screen 420. For instance, for the reagent set which measurement item is "HBsAg" and the lot number is "ZA9999", the remaining quantity (number of measurable times) is zero, and thus red (diagonal lines of narrow interval in the figure) is displayed. For the reagent set which measurement item is "HIV" and the lot number is "QQ0009", the remaining quantity (number of measurable times) is nine times (less than ten times), and thus yellow (diagonal lines of wide interval in the figure) is displayed.

In the set reagent replacement screen 450, the replacement or the retrieval of the reagent set is performed by selecting the replacement button 441 or the retrieval button 442 with the set reagent to be replaced being selected. The operation of replacement or retrieval will be described in detail below.

The individual reagent replacement screen of the R1/R3 reagent and the individual reagent replacement screen of the R2 reagent are similar to the set reagent replacement screen 450 except that the list of reagents not forming a set are displayed, and thus the detailed description will be omitted. In the individual reagent replacement screen, individual reagent can be replaced or retrieved.

Figure 18:
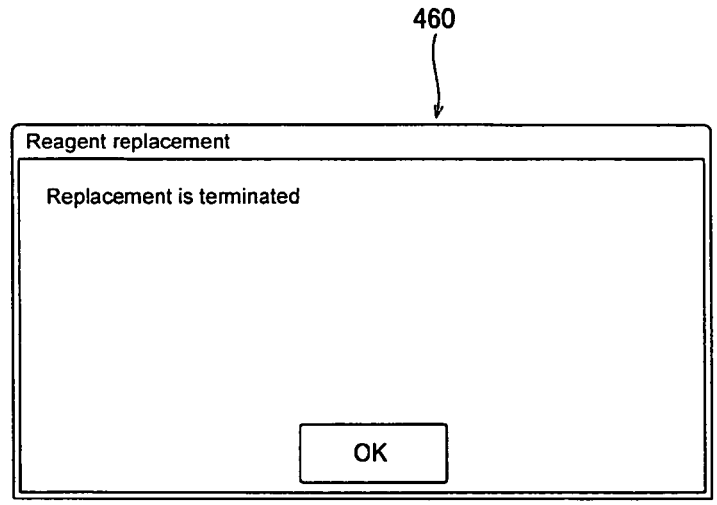
FIG. 18 is a view showing a replacement terminated notification screen.

As shown in FIG. 18, after the replacement or the retrieval of the reagent is terminated, the control device 4 displays a replacement terminated notification screen 460 on the display unit 4b. The user can recognize that the replacement of the reagent is terminated from the replacement terminated notification screen 460.

FIGS. 19 to 22 are views describing the replacement operation of the reagent. The replacement and the retrieval operation of the reagent-containing assemblies 200 and 300 forming a set in the reagent installing unit 7 of the immunological analyzer 1 according to the present embodiment will be described with reference to FIGS. 8, 10, and 19 to 22. In the following description, a case of replacing or retrieving the reagent forming a set will be described.

Figure 19:
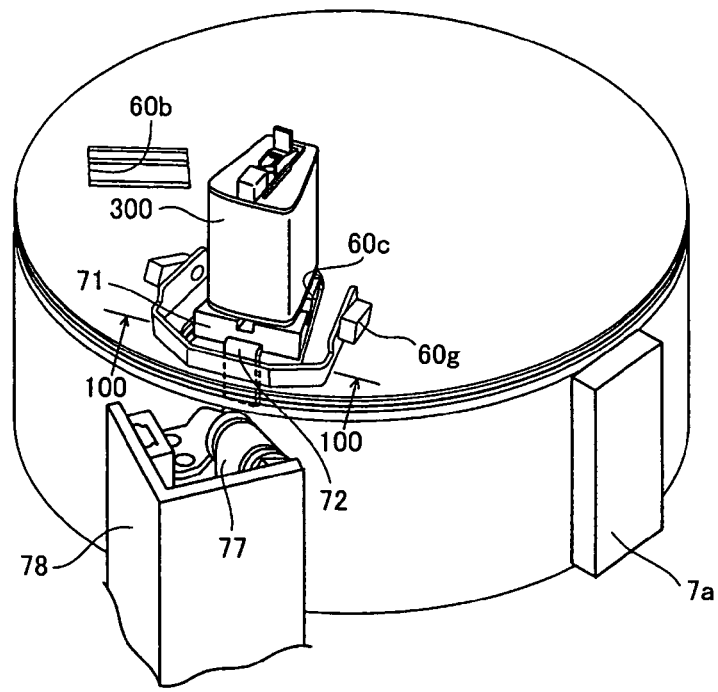
FIG. 19 is a perspective view describing the reagent replacement information.
Figure 20:
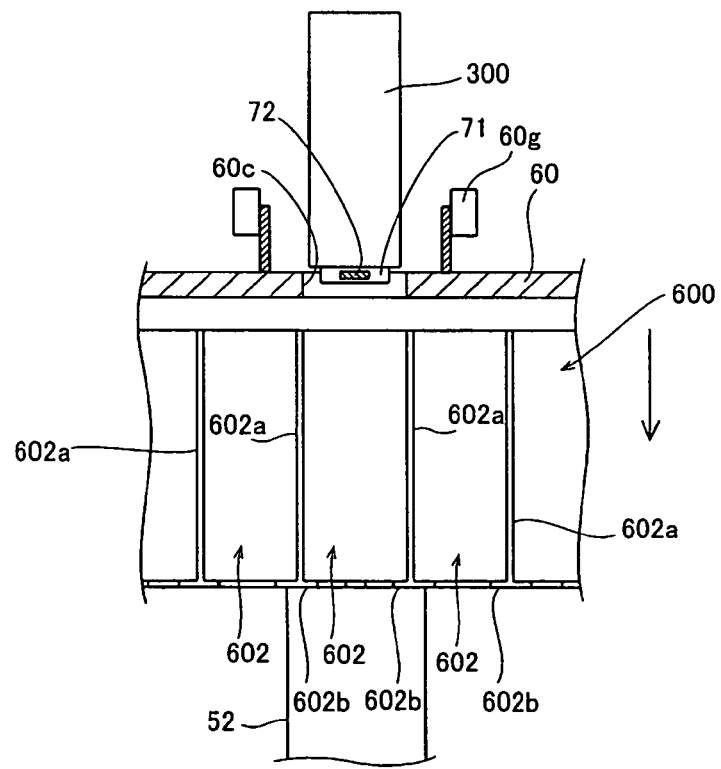
FIG. 20 is a cross sectional view taken along line 100-100 of FIG. 19.

As shown in FIG. 10, the mounting board 71 is arranged at a mounting/retrieving position (sensor 70a is turned ON) in the standby state. Similarly, the mounting board 41 is also arranged at the mounting/retrieving position. When replacing the reagent-containing assemblies 200 and 300, the user first mounts the reagent-containing assemblies 200 and 300 to be added on the mounting board 41 and the mounting board 71, respectively, as shown in FIGS. 19 and 20.

The user instructs replacement of the reagent with the control device 4 in this state. Specifically, the user selects the replacement button 441 with the reagent set to be replaced being selected in the set reagent replacement screen 450. The replacement of the reagent-containing assemblies 200 and 300 forming a set thereby starts.

Figure 21:
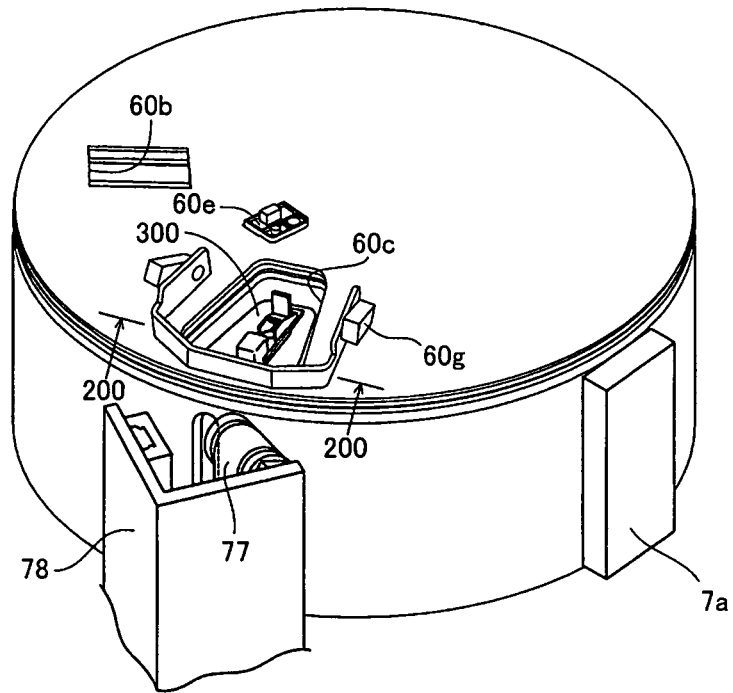
FIG. 21 is a perspective view describing the reagent replacement operation.
Figure 22:
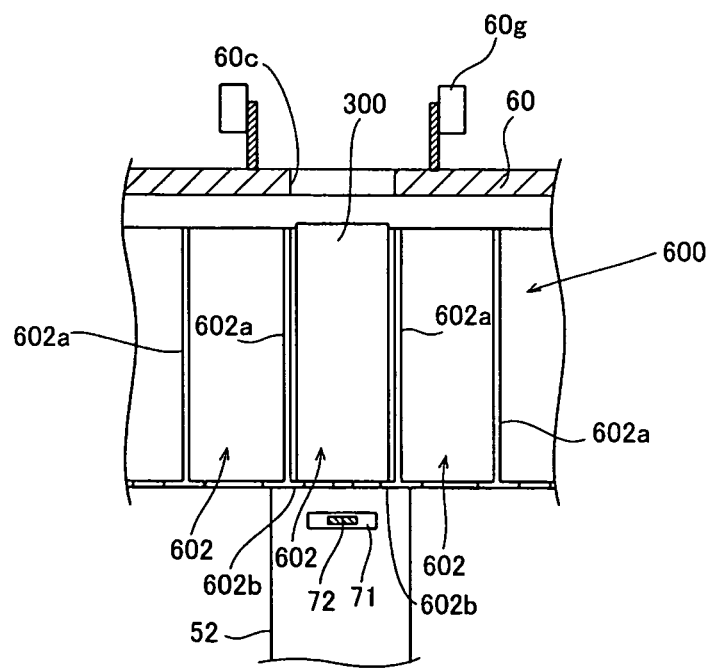
FIG. 22 is a cross sectional view taken along line 200-200 of FIG. 21.

At this point, the rack 600 is rotated by driving the stepping motor 53 (see FIG. 8), and the holder 602 not holding the reagent-containing assembly 300 is moved to below the input/output hole 60c of the lid 60 in the reagent installing unit 7. Thereafter, as shown in FIG. 20, the movement to the lower side of the mounting board 71 is started by driving the motor 76. As shown in FIGS. 21 and 22, when the mounting board 71 passes through the supporting part 602b of the holder 602, the peripheral edge of the bottom surface 323 of the reagent-containing assembly 300 is supported by the supporting part 602b, and the reagent-containing assembly 300 is held by the holder 602.

The driving of the motor 76 is stopped when the detection strip 73b is detected by the sensor 70b. In this state, the rack 600 is rotated by driving the stepping motor 53, and the holder 602 holding the reagent-containing assembly 300 containing the reagent selected in the reagent replacement screen 450 is moved to the standby position on the lower side (upper side of the mounting board 71 at the bottom dead point) of the input/ output hole 60c. The holder holding the reagent-containing assembly 200 accommodating the reagent selected in the reagent replacement screen 450 is also moved to the standby position on the lower side of the input/output hole 30a. In the reagent installing unit 7, the movement of the mounting board 71 to the upper side is started by driving the motor 76. The rising mounting board 71 lifts the reagent-containing assembly 300 supported by the supporting part 602b of the holder 602, and further rises. The mounting board 71 is raised until the sensor 70a detects the detection strip 73b, and is arranged at the mounting/retrieving position. The reagent-containing assembly 300 to be replaced is thereby retrieved outside of the reagent installing unit 7. In the reagent installing unit 6 as well, the reagent-containing assembly 200 to be replaced through similar operation is retrieved outside of the reagent installing unit 6. In the present embodiment, the regent (reagent-containing assembly 200 and reagent-containing assembly 300) forming a set is thereby replaced. After the replacement of the reagent of the set is terminated, the replacement terminated notification screen 460 is displayed on the display unit 4b.

When retrieving the reagent set, the user instructs retrieval of the reagent with the control device 4 with the reagent-containing assembly not mounted on the mounting board 41 and the mounting board 71 arranged at the mounting/retrieving position. That is, in the set reagent replacement screen 450, the user selects the retrieval button 442 with the reagent set to be retrieved being selected. The reagent-containing assemblies 200 and 300 forming a set are thereby retrieved. The operation of retrieval is similar to that of replacement, and thus detailed description will be omitted.

Figure 23:
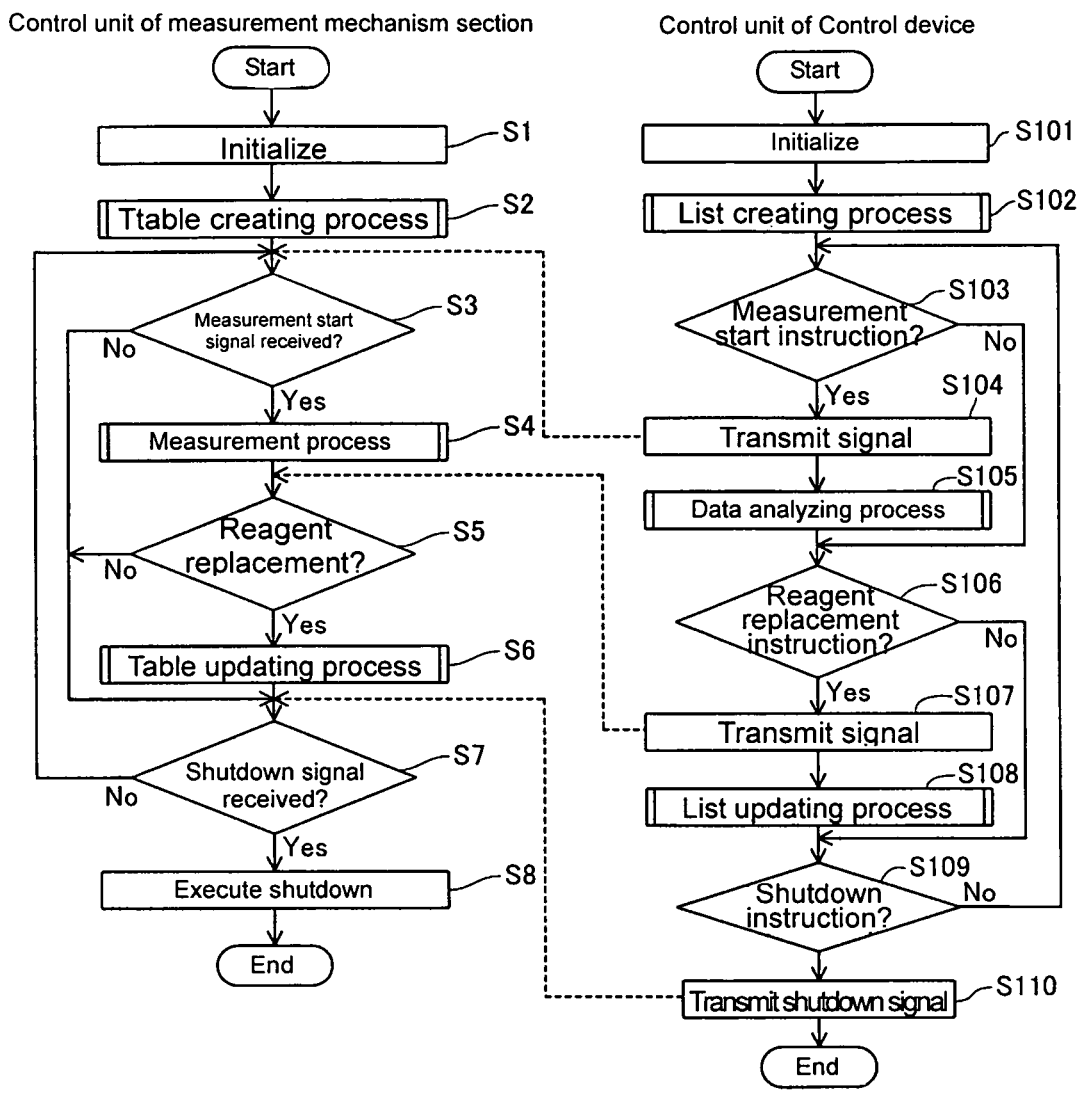
FIG. 23 is a flowchart describing the measurement operation of the immunological analyzer according to one embodiment.

FIG. 23 is a flowchart describing the measurement operation of the control unit of the measurement mechanism section and the control unit of the control device. First, the measurement operation of the immunological analyzer 1 according to one embodiment of the present invention will be described with reference to FIGS. 14, 16, 17, and 23.

First, when the power (not shown) of the measurement mechanism section 2 is turned ON at the control unit 2a of the measurement mechanism section 2, initialization (initialization of program) of the control unit 501 is performed, and operation check of each unit of the measurement mechanism section 2 is performed in step S1. When the power (not shown) of the control device 4 is turned ON, initialization (initialization of program) of the control unit 4a is performed in step S101 in the control unit 4a of the control device 4.

Subsequently, the reagent set table creating process is performed in step S2 in the control unit 2a of the measurement mechanism section 2. The reagent set table creating process will be described in detail below. In the control unit 4a of the control device 4, the reagent registration list creating process is performed in step S102. The reagent registration list creating process will be described in detail below.

The start of measurement is instructed to the control device 4 when the user selects the measurement start button 412 in the reagent arrangement state screen 420 (see FIG. 14) and the measurable item screen 430 (see FIG. 16) of the display unit 4b. In the control unit 4a of the control device 4, determination is made whether or not the instruction to start the measurement is accepted in step S103. The process proceeds to step S106 if instruction to start the measurement is not accepted. If the instruction to start the measurement is accepted, the control unit 4a of the control device 4 transmits the instruction signal to start the measurement to the control unit 2a of the measurement section 2 in step S104. Thereafter, data analyzing process is performed in step S105 in the control unit 4a of the control device 4. The analyzing process will be described in detail below.

In step S3, in the control unit 2a of the measurement mechanism section 2, determination is made on whether or not the signal to start the measurement is received from the control device 4. The process proceeds to step S6 if the signal to start the measurement is not received. If the signal to start the measurement is received, the measurement process is performed in step S4 in the control unit 2a of the measurement mechanism section 2. The measurement process will be described in detail below.

The user selects the replacement button 441 with the reagent set or the individual reagent to be replaced or retrieved being selected in the reagent replacement screen 440 (see FIG. 17) or the individual reagent replacement screen (not shown) to instruct the control device 4 to replace the selected reagent set or the individual reagent.

In the control unit 4a of the control device 4, determination is made on whether or not the instruction to replace the reagent in step S106. The process proceeds to step S109 if the replacement instruction is not accepted. If the replacement instruction is accepted, the control unit 4a of the control device 4 transmits a signal to instruct the replacement of the reagent to the control unit 2a of the measurement mechanism section 2.

The updating process of the reagent registration list involved in the replacement of the reagent is performed in step S108 in the control unit 4a of the control device 4. The updating process of the reagent registration list will be described in detail below.

In the control unit 2a of the measurement mechanism section 2, determination is made on whether or not the signal for instructing reagent replacement is received from the control device 4 in step S5. If the signal for instructing reagent replacement is not received, the process proceeds to step S7. If the signal for instructing reagent replacement is received, the updating process of the reagent set table is performed in step S6. The updating process of the reagent set table will be described in detail below.

The user instructs shutdown in the display unit 4b of the control device 4. At this point, in the control unit 4a of the control device 4, determination is made on whether or not the instruction of shutdown is accepted in step S109. If the instruction of shutdown is not accepted, the process returns to step S103. If the instruction of shutdown is accepted, the control unit 4a of the control device 4 transmits the signal for instructing shutdown to the control unit 2a of the measurement mechanism section 2 in step S110. The measurement operation of the control unit 4a of the control device 4 is terminated in the above manner.

In the control unit 2a of the measurement mechanism section 2, determination is made on whether or not the shutdown signal is received from the control device 4 in step S7. If the shutdown signal is not received, the process returns to step S3. If the shutdown signal is received, the shutdown is executed in step S8. The measurement operation of the control unit 2a of the measurement mechanism section 2 is terminated in this manner.

Figure 24:
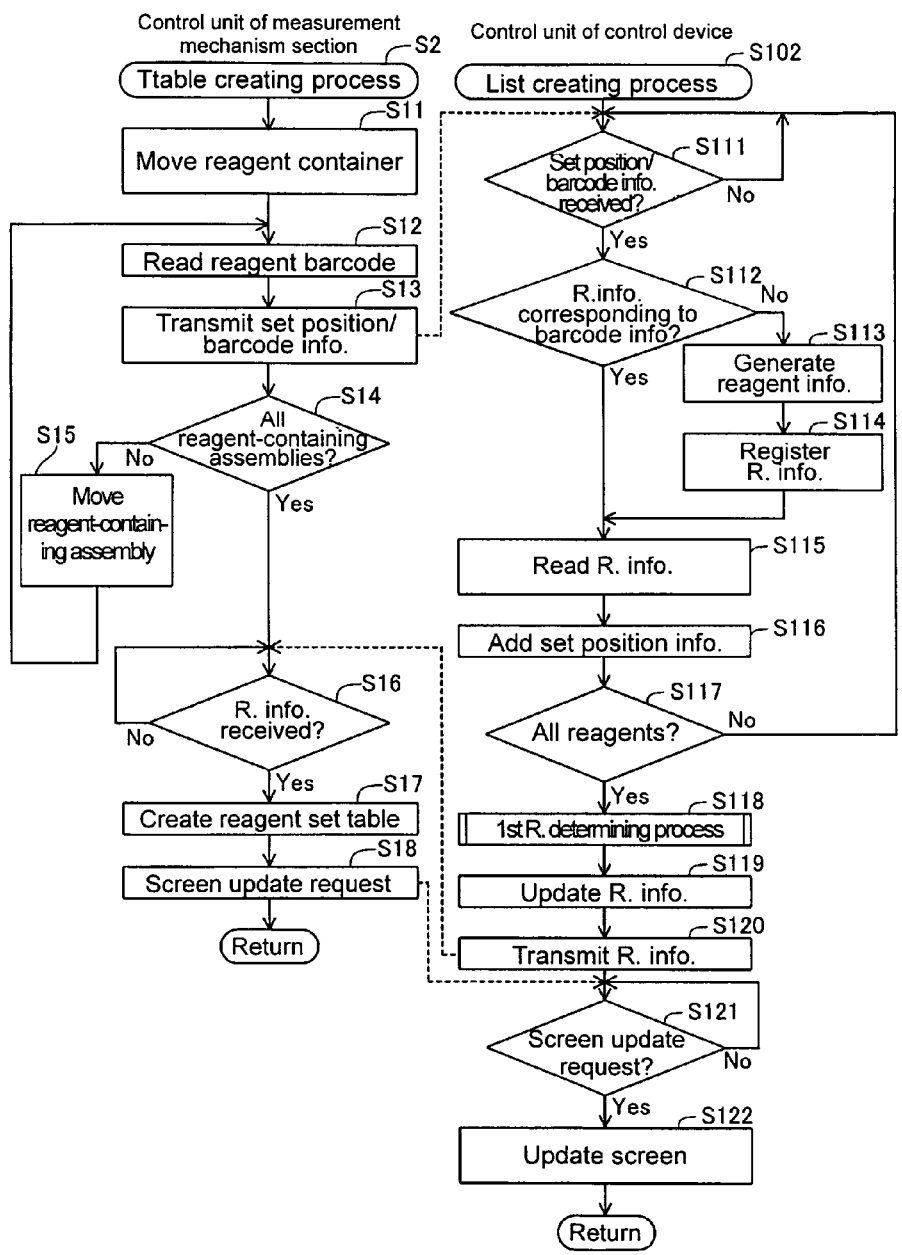
FIG. 24 is a flowchart describing a reagent set table creating process and a reagent registration list creating process shown in FIG. 23.

FIG. 24 is a flowchart describing the reagent set table creating process of the control unit of the measurement mechanism section shown in FIG. 23, and the reagent registration list creating process of the control unit of the control device shown in FIG. 23. The details of the reagent set table creating process in step S2 of FIG. 23 and the reagent registration list creating process in step S102 of FIG. 23 will be described with reference to FIG. 24.

In the reagent set table creating process of the measurement mechanism section 2, first the rack 600 is rotated to move the first reagent container (reagent-containing assembly 300 at the position corresponding to "1" measurement item "HBsAg" of FIG. 14) of the reagent installing unit 7 to the barcode reading position 7b (see FIG. 8) in step S11.

In the control unit 2a of the measurement mechanism section 2, the barcode 300a attached to the side surface of the reagent-containing assembly 300 is read by the barcode reader 7a in step S12. The information (barcode information) recorded on the barcode 300a contains measurement item, lot number, serial number of reagent container, and initial measurable number of times. Thereafter, the control unit 2a of the measurement mechanism section 2 transmits the barcode information acquired by the barcode reader 7a and the set position information of the reagent to the control unit 4a of the control device 4 in correspondence to each other in step S13.

Subsequently, in the control unit 2a of the measurement mechanism section 2, determination is made on whether or not reading and transmission of the barcode information of step S12 and step S13 are performed on all the reagent-containing assemblies 300 installed in the reagent installing unit 7 in step S14. If the process is not performed on all the reagent-containing assemblies 300, in the control unit 2a of the measurement mechanism section 2, the rack 600 is rotated to move the reagent-containing assembly 300 of the next (second) set position to the barcode reading position 7b in step S15, and the processes of step S12 and step S13 are performed on the reagent-containing assembly 300 of the second set position. Similarly, the processes of step S12 and S13 are performed on the third to the $N^{th}$ reagent-containing assemblies 300.

In the control unit 4a of the control device 4, determination is first made on whether or not the set position information and the barcode information are received from the control unit 2a of the measurement mechanism section 2 in step S111. This determination is repeated if the information is not received. If the information is received, determination is made on whether or not the reagent information corresponding to the barcode information is in the reagent DB in the control unit 4a of the control device 4 in step S112. That is, determination is made on whether or not the previous data (reagent information) in measurement stored in the control device 4 and the barcode information reread after activation of the apparatus match. If the reagent information corresponding to the barcode information is in the reagent DB, the process proceeds to step S115. If the reagent information corresponding to the barcode information is not in the reagent DB, this means that the reagent-containing assembly having the relevant barcode information is not present in the previous measurement, and thus the barcode information is analyzed in the control unit 4a of the control device 4 in step S113 to generate the reagent information of the reagent of the reagent-containing assembly. In the control unit 4a of the control device 4, the reagent information generated in step S113 is registered in the reagent DB in step S114.

Thereafter, in the control unit 4a of the control device 4, the reagent information corresponding to the barcode information received in step S111 is read from the reagent DB in step S115, and the set position information is added to the reagent information in step S116.

Subsequently, in the control unit 4a of the control device 4, determination is made on whether or not step S111 to step S116 are terminated for all the reagents (reagent-containing assemblies) installed in the reagent installing units 6 and 7 in step S117. If the processes are not terminated on all the reagents, the process returns to step S111. If the processes are terminated on all the reagents, a first usable reagent determining process for determining the reagent forming a set is performed in step S118 in the control unit 4a of the control device 4. The first usable reagent determining process will be described in detail below.

Thereafter, in the control unit 4a of the control device 4, the respective serial number of the reagent-containing assembly (reagent which measurement item can be measured) forming a set is added to the reagent information of the reagent DB and updated in step S119. In the control unit 4a of the control device 4, thereafter, the reagent information after updating is transmitted to the control unit 2a of the measurement mechanism section 2 in step S120.

If the above processes are terminated for all the reagent-containing assemblies 300 in step S14, determination is made on whether or not the reagent information is received from the control device 4 in step S16 in the control unit 2a of the measurement mechanism section 2. The reagent information contains, in addition to the barcode information, information on the number of measurable times at the current point, presence or absence of the opponent forming the set, serial number of the reagent-containing assembly 300 accommodating the reagent of the opponent forming the set, and usage priority. If the reagent information is not received, the determination is repeated. If the reagent information is not received, the reagent set table is created based on the reagent information received in step S16 in step S17 in the control unit 2a of the measurement mechanism section 2.

In the control unit 2a of the measurement mechanism section 2, an update request signal for requesting update of the screen of the display unit 4b of the control device 4 is transmitted to the control unit 4a of the control device 4 in step S18. The reagent set table creating process is carried out in such manner. The reagent installed in the reagent installing unit 7 has been described in the above description, but the reagent set table creating process is similarly performed on the reagent installed in the reagent installing unit 6.

In the control unit 4a of the control device 4, determination is made on whether or not the update request signal of the screen is received in step S121. If the update request signal of the screen is not received, the determination is repeated. If the update request signal of the screen is received, the reagent arrangement state screen 420 and the measurable reagent screen 430 are updated in step S122 in the control unit 4a of the control device 4. The reagent registration list creating process is performed in the above manner.

Figure 25:
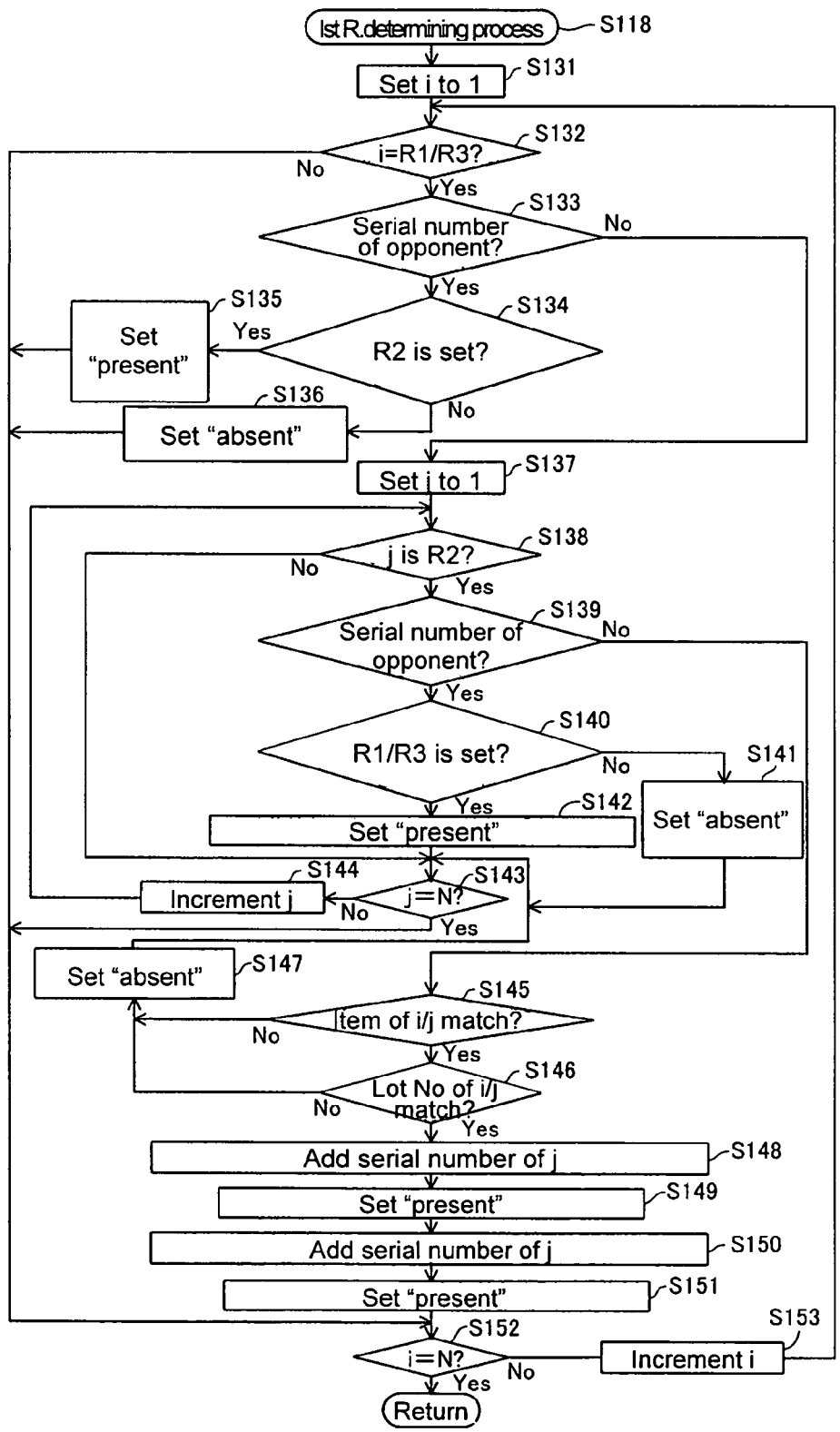
FIG. 25 is a flowchart describing a first usable reagent determining process shown in FIG. 24.

FIG. 25 is a flowchart describing the first usable reagent determining process of the control unit of the control device shown in FIG. 24. The details of the first usable reagent determining process in step S1118 of FIG. 24 will be described with reference to FIG. 25.

In the first usable reagent determining process, a number i (i is an integer greater than or equal to one and lower than or equal to N) representing the set position of the reagent-containing assembly 300 in the reagent installing unit 7 is first set to i=1 in step S131. In the present embodiment N=13 is met.

In the control unit 4a of the control device 4, determination is made on whether or not the reagent (hereinafter referred to as reagent "i=1") accommodated in the reagent-containing assembly 300 where set position in the reagent installing unit 7 is "1" is R1/R3 reagent in step S132. If the reagent "i=1" is not R1/R3 reagent, the process proceeds to step S152. If the reagent "i=1" is R1/R3 reagent, determination is made on whether or not the serial number of the opponent reagent forming a set is contained in the reagent information of reagent "i=1" in step S133 in the control unit 4a of the control device 4. If the serial number of the opponent is contained in the reagent information, determination is made on whether or not the R2 reagent (reagent-containing assembly 300) specified by the relevant serial number is installed in the reagent installing unit 7 in step S134. If the R2 reagent is installed, the presence or absence of the opponent forming the set is set to "present" of the reagent information of the reagent "i=1" in step S135, and the process proceeds to step S152. If the R2 reagent is not installed, or opponent's serial number is not contained in the reagent information, the presence or absence of the opponent forming the set is set to "absent" of the reagent information of the reagent "i=1" in step S136, and the process proceeds to step S152.

If the opponent's serial number is not contained in the reagent information in step S133, the number j (j is an integer greater than or equal to 1 and lower than or equal to N) representing the set position of the reagent-containing assembly in the reagent installing unit 6 is set to j=1 in step S137 in the control unit 4a of the control device 4.

In the control unit 4a of the control device 4, determination is made on whether or not the reagent (hereinafter referred to as reagent "j=1") accommodated in the reagent-containing assembly 200 which set position in the reagent installing unit 6 is "1" is R2 reagent in step S138. If the reagent "j=1" is not R2 reagent, the process proceeds to step S143. If the reagent "j=1" is R2 reagent, determination is made on whether or not the serial number of the opponent reagent forming a set is contained in the reagent information of reagent "j=1" in step S139 in the control unit 4a of the control device 4. If the serial number of the opponent is not contained in the reagent information, the process proceeds to step S145.

If the serial number of the opponent is contained in the reagent information in step S139, determination is made on whether or not the R1/R3 reagent (reagent-containing assembly 200) specified by the serial number of the relevant opponent is installed in the reagent installing unit 6 in step S140 in the control unit 4a of the control device 4. If the R1/R3 reagent is installed in the reagent installing unit 6, the presence or absence of the opponent is set to "present" of the reagent information of the reagent "j=1" in step S142, and the process proceeds to step S143. If the reagent-containing assembly 200 specified by the serial number is not installed in step S140, the presence or absence of the opponent is set to "absent" of the reagent information of the reagent "j=1" in step S141, and the process proceeds to step S143.

In step S143, determination is made on whether or not j=N is met. If j=N is not met, the value of j is incremented in step S144. That is, j=2 is set. Thereafter, step S138 to step S144 are repeated until j=N is met. If j=N is met in step S143, the process proceeds to step S152.

In step S145, determination is made on whether or not the analysis items of the reagent "i" and the reagent "j" match. If the analysis items of the reagent "i" and the reagent "j" do not match, the presence or absence of opponent of the reagent information of the reagent "i" and the reagent "j" is set to "absent" in step S147, and the process proceeds to step S143. If the analysis items of the reagent "i" and the reagent "j" match, determination is made on whether or not the lot numbers of the reagent "i" and the reagent "j" match in step S146. If the lot numbers of the reagent "i" and the reagent "j" do not match, the presence or absence of opponent of the reagent information of the reagent "i" and the reagent "j" is set to "absent" in step S147, and the process proceeds to step S143. If the lot numbers of the reagent "i" and the reagent "j" match, determination is made that the reagent "i" and the reagent "j" form a set, and the process proceeds to step S148.

In step S148, the serial number of the reagent "j" is added as the serial number of the opponent forming a set to the reagent information of the reagent "i". The presence or absence of opponent is set to "present" of the reagent information of the reagent "i" in step S149. In step S150, the serial number of the reagent "i" is added as the serial number of the opponent forming a set to the reagent information of the reagent "j". In step S151, the presence or absence of the opponent is set to "present" of the reagent information of the reagent "j".

Subsequently, in step S152, determination is made on whether or not i=N is met. If i=N is not met, the value of i is incremented in step S153, and the process proceeds to step S132. Step S132 to step S153 are repeated until i=N is met. If i=N is met in step S152, the first usable reagent determining process is terminated.

In the first usable reagent determining process, determination is made on whether the analysis item and the lot number match for all the combinations of the plurality of reagents accommodated in the reagent installing unit 6 and the plurality of reagents accommodated in the reagent installing unit 7 to determine the reagent "i" and the reagent "j" forming the set. The respective serial number is added to the reagent information of the reagent "i" and the reagent "j" determined to form the set. For the reagent "i" and the reagent "j" determined that the analysis item does not match or the lot number does not match, the presence or absence of the opponent's reagent forming the set is set to "absent" for each of the reagent "i" and the reagent "j" in the reagent registration list. The reagent "i" and the reagent "j" are thereby prohibited from being registered as a reagent set.

Figure 26:
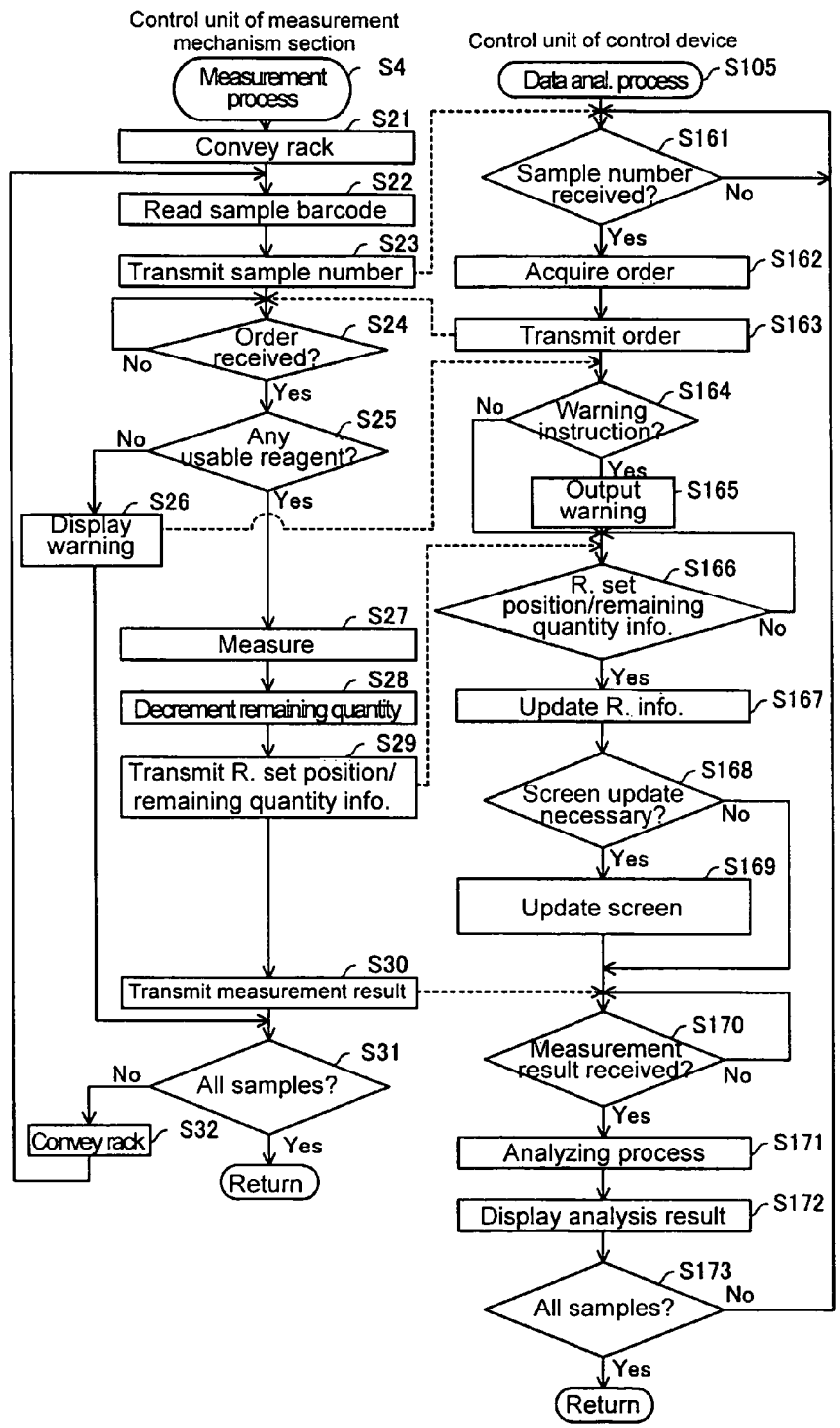
FIG. 26 is a flowchart describing a measurement process and a data analyzing process shown in FIG. 23.

FIG. 26 is a flowchart describing the measurement process of the control unit of the measurement mechanism section shown in FIG. 23 and the data analyzing process of the control unit of the control device shown in FIG. 23. The details of the measurement process in step S4 of FIG. 23 and the data analyzing process in step S105 of FIG. 23 will be now described with reference to FIGS. 1, 2, and 26.

First, in the control unit 2a of the measurement mechanism section 2, the rack 101 accommodating the sample is conveyed in step S21, and moved to the sample aspirating position 1a (see FIGS. 1 and 2). In step S22, the barcode attached to the test tube 100 accommodating each sample is read by the barcode reader (not shown) when the rack 101 is conveyed. In the control unit 2a of the measurement section 2, the sample number recorded on the barcode is transmitted to the control unit 4a of the control device in step S23.

In the control unit 4a of the control device 4, determination is first made on whether or not the sample number is received from the control unit 2a of the measurement mechanism section 2 in step S161. If the sample number is not received, the determination is repeated. If the sample number is received, an order is acquired in step S162. The order is information containing the analysis item in correspondence with information specifying the sample. According to such order, the measurement mechanism section 2 recognizes which measurement item of which sample measure. The order is registered in a host computer (not shown) connected to the control device 4 or is stored in the control device 4 by being manually input by the user. After acquiring the barcode information of the sample, the control device 4 searches for the relevant one from the order stored therein and acquires the order by inquiring the host computer with the sample ID as a key. Thereafter, the control unit 4a of the control device 4 transmits the order to the control unit 2a of the measurement mechanism section 2 in step S163.

In the control unit 2a of the measurement mechanism section 2, determination is made on whether or not the order is received in step S24. If the order is not received, the determination is repeated.

If the order is received, determination is made on whether or not a reagent set appropriate for performing the measurement of the analysis item corresponding to the relevant order exists based on the reagent set table stored in the control unit 2a in step S25. If determined that an appropriate reagent set exists, the process proceeds to step S27, and the measurement is carried out. That is, the quantity of the antigen contained in the sample is measured based on the order by using the set of R1/R3 reagent and R2 reagent, the R4 reagent and the R5 reagent.

If determined that the reagent set appropriate for performing the measurement of the analysis item corresponding to the relevant order does not exist in step S25, the reagent not forming the reagent set is prohibited from being used in the measurement, and thus the process does not proceed to step S27. Instead, the process proceeds to step S26, and a warning instruction is transmitted to the control unit 4a of the control device 4 to display a warning to the user. The process thereafter proceeds to step S31 to be described below.

Figure 28:
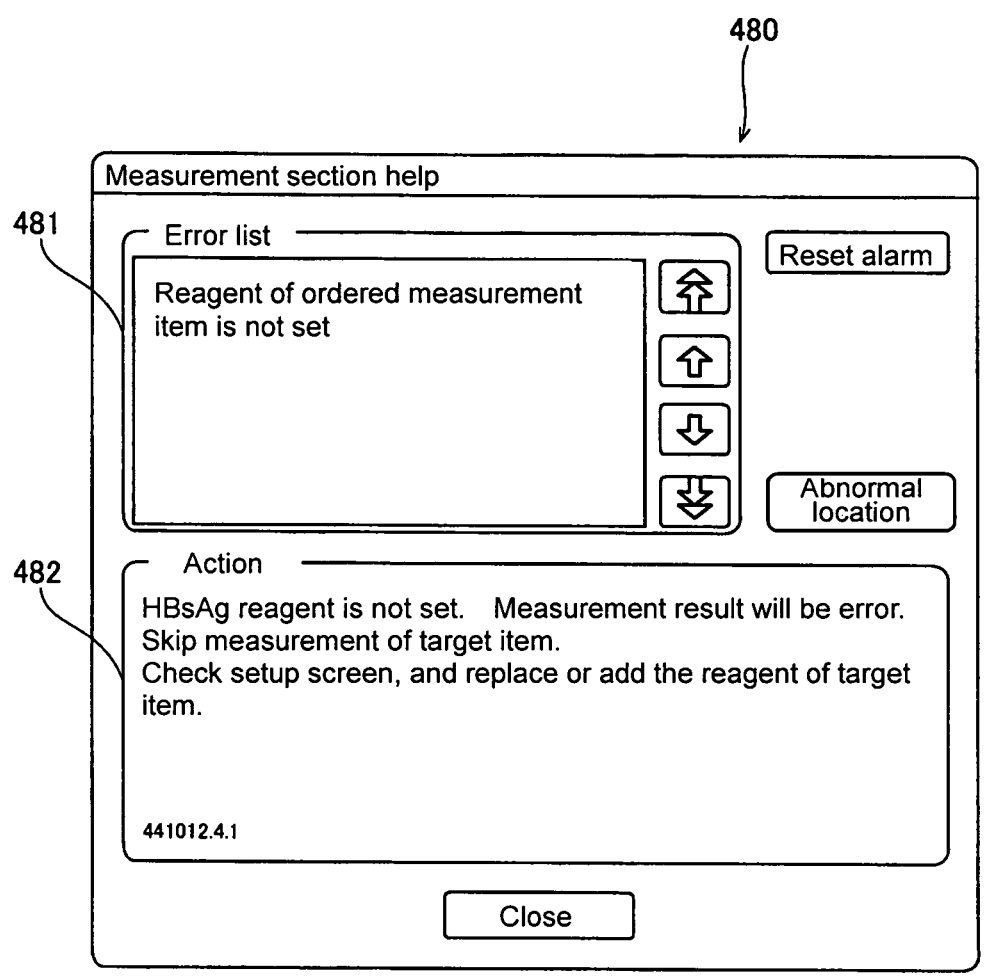
FIG. 28 is a view showing a warning screen.

The control unit 4a of the control device 4 determines whether or not the warning instruction is received from the control unit 2a of the measurement mechanism section 2 in step S164. If the warning instruction is not received, the process proceeds to step S166 to be described below. If the warning instruction is received, a warning screen warning that the reagent set appropriate for performing the measurement of the analysis item corresponding to the order does not exist is displayed on the display unit 4b in step S165. An example is shown in FIG. 28. The warning screen 480 includes a warning content display region 481 showing the content of the warning, and an explanation region 482 showing the explanation on the warning and the method of responding to the warning. In the present example, display is made in the warning content display region 481 that a useable reagent set corresponding to the order is absent. In the explanation region 482, display is made that the usable reagent set is absent for the HBsAg of the analysis items. The warning screen 480 is displayed with preference on the front of the reagent management screen 410, the reagent arrangement state screen 420, and the like even if such other screens are displayed on the display unit 4b.

Thereafter, the remaining quantity (number of measurable times) of the used reagent is decremented in step S28. In step S29, the remaining quantity information after decrement in step S28 of the used reagent is transmitted to the control unit 4a of the control device 4 in correspondence to the set position information in step S29.

In the control unit 4a of the control device 4, determination is made on whether or not the remaining quantity information and the set position information are received in step S166. If the remaining quantity information and the set position information are not received, the determination is repeated. If the remaining quantity information and the set information are received, the reagent information of the relevant reagent is updated based on the received information in step S167.

In the control unit 4a of the control device 4, determination is made on whether or not update of screen is necessary in step S168. That is, when the remaining quantity of the reagent decreases with measurement, determination is made on whether or not a warning (turn the mark yellow or red) is necessary in the reagent arrangement state screen 420. Specifically, determination is made on whether or not the measurable number of times is greater than or equal to ten times, greater than or equal to one time and less than or equal to nine times, or zero time. If update of the screen is not necessary, the process proceeds to step S170. If the update of the screen is necessary, the reagent arrangement state screen and the measurable reagent screen are updated in step S169. That is, when the measurable number of times decreases from ten times to nine times, and decreases from one time to zero time, the color of the mark is updated from white to yellow and from yellow to red.

Subsequently, in the control unit 2a of the measurement mechanism section 2, the measurement result is transmitted to the control unit 4a of the control device 4 in step S30. Determination is made on whether or not the measurement is terminated for all the samples based on the order in step S31. If measurement on all the samples is not terminated, the rack 101 accommodating the sample is further conveyed in step S32, and the process proceeds to step S22. Thereafter, step S22 to step S32 are repeated until the measurement on all the samples is terminated. If determined that the measurement all the samples is terminated in step S31, the measurement process of the control unit 2a of the measurement mechanism section 2 is terminated.

In the control unit 4a of the control device 4, determination is made on whether or not the measurement result is received from the control unit 2a of the measurement mechanism section 2 in step S170. If the measurement result is not received, the determination is repeated. If the measurement result is received, the analyzing process is performed based on the measurement result in step S171. Thereafter, the control unit 4a of the control device 4 displays the analysis result on the display unit 4b in step S172. Determination is made on whether or not the analysis is performed on all the samples in step S173. If analysis is not performed on all the samples, the process proceeds to step S161, and step S161 to step S173 are repeated until analysis is performed on all the samples. When determined that the analysis is performed on all the samples in step S173, data analyzing process by the control unit 4a of the control device 4 is terminated.

Figure 27:
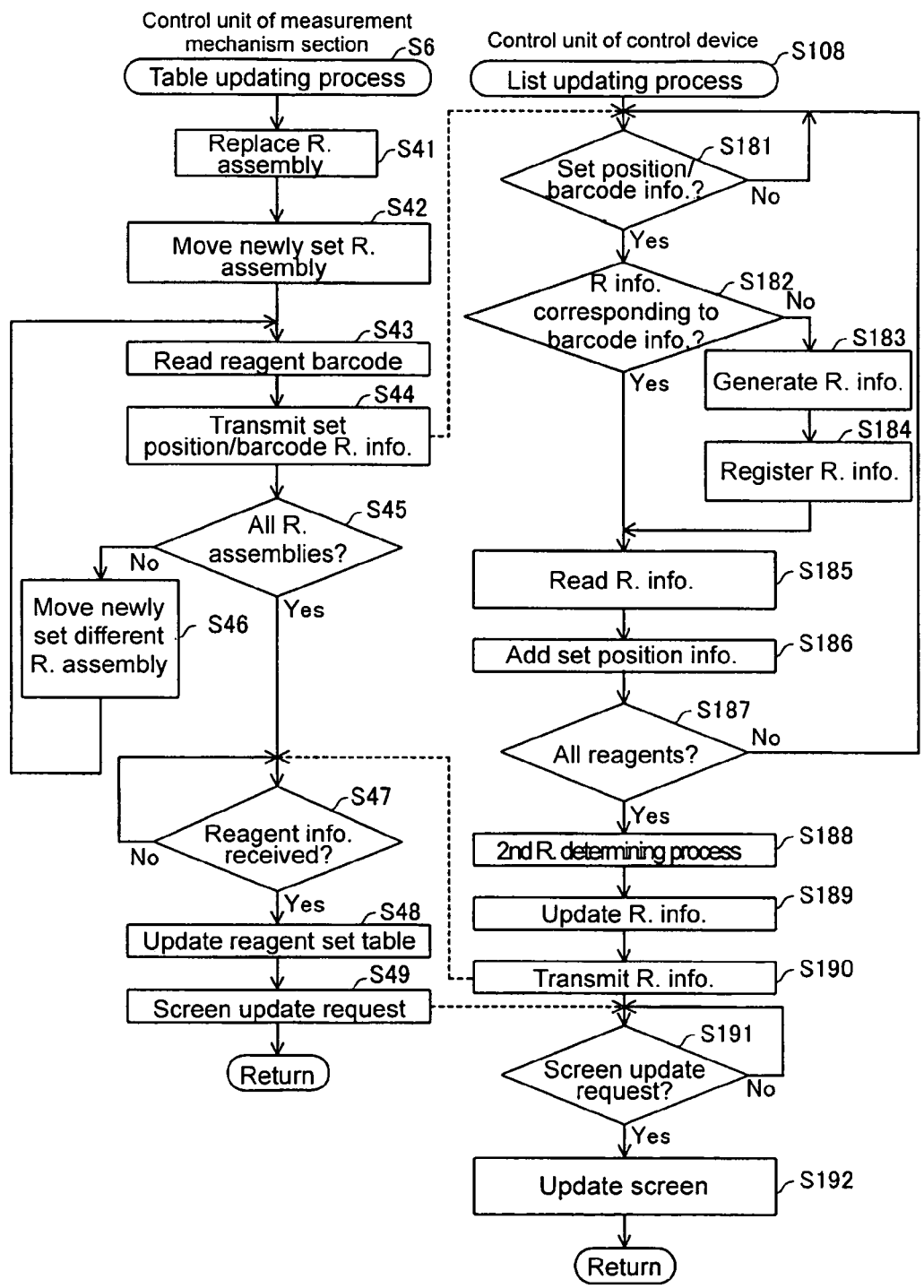
FIG. 27 is a flowchart describing a reagent set table updating process and a reagent registration list updating process shown in FIG. 23.

FIG. 27 is a flowchart describing the reagent set table updating process of the control unit of the measurement section shown in FIG. 23 and the reagent registration list updating process of the control unit of the control device shown in FIG. 23. The details of the reagent set table updating process in step S6 of FIG. 23 and the reagent registration list updating process in step S108 of FIG. 23 will be now described with reference to FIG. 27. A case of replacing the reagent will be described.

In the reagent set table updating process, the reagent is first replaced in step S41.

In the reagent installing unit 7, the newly set (added) reagent-containing assembly 300 is moved to a barcode reading position 7b in step S42. Similar to step S12 and step S13, the barcode 300a of the reagent-containing assembly 300 is read and the barcode information is transmitted to the control unit 4a of the control device 4 in association with the position information of the reagent-containing assembly 300 in step S43 and step S44.

If a plurality of reagent-containing assemblies 300 is added, determination is made on whether or not transmission of the barcode information and the position information is performed for all the added reagent-containing assemblies 300 in step S45. If transmission of the barcode information and the position information is not performed for all the added reagent-containing assemblies 300, the reagent installing unit 7 is driven to move the newly set (added) reagent-containing assembly 300 to the barcode reading position 7b in step S46. Step S43 to step S46 are repeated until the transmission of the barcode information and the position information is performed for all the added reagent-containing assemblies 300.

In the control unit 4a of the control device 4, determination is made on whether or not the set position information and the barcode information of the replaced reagent are received from the control unit 2a of the measurement mechanism section 2 in step S181. If the information is not received, the determination is repeated. If the information is received, determination is made on whether or not the reagent information corresponding to the barcode information is in the reagent DB in step S182, similar to step S1112 of FIG. 24, in the control unit 4a of the control device 4. If the reagent information corresponding to the barcode information is in the reagent DB, the process proceeds to step S185. If the reagent information corresponding to the barcode information is not in the reagent DB, processes similar to step S113 and step S114 of FIG. 24 are performed in step S183 and step S184.

Thereafter, in the control unit 4a of the control device 4, processes similar to step S115 and step S116 of FIG. 24 are performed in step S185 and step S186.

In the control unit 4a of the control device 4, determination is made on whether or not step S181 to step S186 are terminated for all the replaced reagents (reagent-containing assemblies) in step S187. If not terminated for all the reagents, the process returns to step S181. If terminated for all the reagents, a second usable reagent determining process of a process similar to the first usable reagent determining process shown in FIG. 25 is performed on the replaced reagent in step S188 in the control unit 4a of the control device 4. In the control unit 4a of the control device 4, update of the reagent information and transmission of the reagent information to the control unit 2a of the measurement mechanism section 2 are performed in step S189 and step 190, similar to step S119 and step S120 of FIG. 24.

Subsequently, in the control unit 2a of the measurement mechanism section 2, determination is made on whether or not the reagent information of the replaced reagent is received from the control unit 4a of the control device 4 in step S47. If not received, the determination is repeated. If received, the reagent set table is updated based on the received reagent information in step S48. Thereafter, the update request signal of the screen is transmitted to the control unit 4a of the control device 4 in step S49, similar to step S18 of FIG. 24. The updating process of the reagent set table by the control unit 2a of the measurement mechanism section 2 is performed in the above manner. The case for the reagent installing unit 7 has been described above, but similar process is also performed in the reagent installing unit 6.

In the control unit 4a of the control device 4, determination is made on whether or not the screen update request is received, and update of the reagent arrangement state screen 420 and the measurable item screen 430 is performed for the replaced reagent in step S191 and step S192, similar to step S121 and step S122 of FIG. 24. The updating process of the reagent registration list is performed in the above manner.

In the present embodiment, a combination of the reagent accommodated in a predetermined reagent-containing assembly 200 of the plurality of reagent-containing assemblies 200 and the reagent accommodated in a predetermined reagent-containing assembly 300 of the plurality of reagent-containing assemblies 300 is registered as a set based on the reagent information read by the barcode readers 6a and 7a, so that a combination of the reagent held in the reagent installing unit 6 and the reagent held in the reagent installing unit 7 is automatically managed as a set. Accordingly, a plurality of reagents respectively held at two holding locations can be easily managed as reagents necessary for the same analysis item.

In the present embodiment, the reagents which analysis item and lot number correspond to each other are registered as a set as described above, so that the correspondence relation of not only the analysis item but the lot number can also be determined, whereby analysis is performed with the reagents having the same lot number and the measurement result can be more accurately obtained. That is, when manufacturing and shipping the reagent related to the analysis item in which the measurement is performed by using a plurality of types of reagents, the manufacturer of the reagent performs a check test of the reagent performance with the combination having the same lot number with respect to a plurality of types of reagents, and ships the same. Therefore, when analyzing the sample by using the shipped reagent on the sample analyzer, the reliability of the measurement result further enhances if the reagent having the same lot number is used in combination for the analysis item in which measurement is performed by using a plurality of types of reagents.

In the present embodiment, when registering the combination of reagents as a set, the reagents forming a set are managed by the serial number without redundant numbers by registering the correspondence relation of the serial number information, whereby measurement by combination other than the combination of the registered set is prevented from being performed.

In the present embodiment, the reagent arrangement state screen 420 showing the arrangement state of the plurality of reagent-containing assemblies 200 and 300 held in the reagent installing units 6 and 7, respectively, is displayed on the display unit 4, so that the user can recognize the arrangement state of the reagent-containing assembly by looking at the display unit 4b.

In the present embodiment, the reagent not forming a set is displayed in an identifiable manner from the reagent forming a set, so that the user can recognize the reagent not forming a set by looking at the display unit 4b. The reagent not forming a set recognized on the display unit 4b can be replaced or retrieved, and thus the reagents can be easily managed.

The embodiment disclosed herein is merely illustrative in all aspects and should not be recognized as being exclusive. The scope of the invention is defined by the scope of the claims rather than by the description of the embodiment, and meaning equivalent to the claims and all modifications within the scope is encompassed herein.

For instance, in the embodiment, an example of installing the reagent in two reagent installing units of the reagent installing unit 6 and the reagent installing unit 7 has been described, but the present invention is not limited thereto, and may be installed in three or more reagent installing units. Alternatively, a plurality of types of reagents may be installed in one reagent installing unit.

In the embodiment, an example of separately arranging the first reagent installing unit (reagent installing unit 6) for installing the R1/R3 reagent and the second reagent installing unit (reagent installing unit 7) for installing the R2 reagent has been described, but the present invention is not limited thereto, and one reagent installing unit may have the functions of the first reagent installing unit and the second reagent installing unit.

In the above described embodiment, an example of separately arranging the first barcode reader (barcode reader 6a) for reading the barcode of the R1/R3 reagent and the second barcode reader (barcode reader 7a) for reading the barcode of the second reagent has been described, but the present invention is not limited thereto, and one barcode reader may have the functions of the first barcode reader and the second barcode reader.

In the above described embodiment, when determined that the reagent set appropriate for performing the measurement of the analysis item corresponding to the order does not exist in the control unit 2a of the measurement mechanism section 2, the reagent not forming the reagent set is prohibited from being used in the measurement. This includes determining whether or not the R1/R3 reagent exists, or whether or not the R2 reagent corresponding to the analysis item exists for the ordered analysis item, and prohibiting the measurement of the analysis item if either the R1/R3 reagent or the R2 reagent is lacking. If both the R1/R3 reagent and the R2 reagent exist, determination is made on whether or not the lot number thereof matches, if the lot number of the R1/R3 reagent and the lot number of the R2 lot number do not match, such reagents are prohibited from being combined and used in the measurement of the analysis item.

Furthermore, in the above described embodiment, an example of notifying the user with the replacement terminated notification screen 460 displaying that replacement or retrieval of the reagent is terminated on the display unit 4b has been described, but the present invention is not limited thereto, and an indicator that emits light when the replacement or the retrieval of the reagent is terminated may be arranged in the measurement mechanism section or notification may be made by sound such as voice.

In the above described embodiment, a case of warning the user the notice to prohibit the measurement of the measurement item through the warning screen 480 if determined that the reagent set appropriate for performing the measurement corresponding to the order does not exist has been described, but the present invention is not limited thereto, and an indicator that emits light when the appropriate reagent set does not exist may be arranged in the measurement mechanism section or notification may be made by sound such as voice.

In the above described embodiment, a configuration of lowering the mounting board 41 and the mounting board 71 to the standby position of the respective reagent holder when the replacement of the set of the reagent combination is instructed so that the new reagent-containing assemblies 200 and 300 arranged on the mounting board 41 and the mounting board 71 are respectively conveyed to the two reagent holders, rotation moving the reagent holder so that the reagent-containing assemblies 200 and 300 to be replaced moves to the standby position of the respective reagent holder, and raising the mounting board 41 and the mounting board 71 from the standby position of the respective reagent holder so that the reagent-containing assemblies 200 and 300 to be replaced are automatically conveyed outside of the reagent holder has been described, but the present invention is not limited thereto, and the user can put in or take out the reagent-containing assembly by hand task with respect to the reagent holder without arranging a mounting board for putting in and taking out the reagent-containing assembly with respect to the reagent holder and a mechanism for raising and lowering the same. In such configuration, when replacement of the reagent set to be replaced is instructed, the reagent holder is rotation moved so that the two reagent-containing assemblies are moved to a predetermined put in/take out position of the respective holder, and the user takes out the reagent-containing assembly at the put in/take out position and arranges a new reagent-containing assembly at the put in/take out position, thereby replacing the reagent. When the retrieval of the reagent set is instructed, the reagent holder rotatably moves so that the user retrieves the reagent-containing assembly moved to the put in/take out position of the respective reagent holder.

In the embodiment described above, when measuring a predetermined analysis item in the immunological analyzer 1, the matching of the lot number of the R1/R3 reagent (R1 is capture antibody reagent, R3 is labeled antibody reagent) and the lot number of the R2 reagent (R2 is magnetic particle reagent) is monitored, and such reagents are registered as reagent set when the lot numbers match. However, the type and combination of the reagents which matching of the lot number is to be monitored are not limited thereto. For instance, in the immunological analyzer 1, various reagents such as capture antibody (R1) that bonds and captures the antigen to be measured, magnetic particles (R2), labeled antibody (R3), dispersion liquid (R4), and light emitting substrate (R5) are used. The matching of lot numbers may be monitored for the combination of an arbitrary type of reagent in which enhancement of measurement accuracy is expected by using combination of reagents having the same lot number of the above reagents in the measurement.

In the above described embodiment, since the measurement object is an antigen, an example of having the capture reagent (R1) for capturing the antigen as the antibody reagent has been described, but the present invention is not limited thereto, and if the measurement object is an antibody, the capture reagent may be an antigen reagent. Similarly, the labeled antibody (R3) may be a labeled antigen.

In the above described embodiment, a case of applying the present invention to the immunological analyzer 1 has been described, but the present invention is not limited thereto and may be applied to other analyzers such as a biochemical analyzer, a blood coagulation analyzer, and the like including one or a plurality of reagent installing units. The present invention may be also applied to a hematology analyzer. As a reagent for the hematology analyzer, diluent for diluting the blood sample, red blood cell hemolyzing agent for hemolyzing red blood cells, white blood cell hemolyzing agent for damaging the cell membrane of a specific type of white blood cell, a staining fluid for staining a specific blood cell, or the like is known. In the hematology analyzer applied with the flow cytometry, sheath fluid for flowing as if enveloping the periphery of the sample liquid flow in the flow cell is used.

The matching of the lot numbers may be monitored for the combination of an arbitrary type of reagent in which enhancement of measurement accuracy is expected by using combination of reagents having the same lot number of the above reagents in the measurement.

In the above described embodiment, if the lot number of the different type of reagents matches, such reagents are combined and used as a reagent set. However, not limited to the lot number, the identification information arbitrarily assigned to each reagent by the manufacturer of the regent may be used. The manufacturer of the reagent can define in advance the combination of the identification information of the reagent to form the combination set, and use the reagents corresponding to the relevant combination in the measurement.

It should be apparent to those skilled in the art that the present invention may be embodied in many other specific forms without departing from the spirit or scope of the invention. Therefore, the present invention is not to be limited to the details given herein, but may be modified within the scope and equivalence of the appended claims.

The invention claimed is:

1. A sample analyzer for analyzing a sample by using a first reagent and a second reagent comprising:

a first reagent container holder capable of holding a first reagent container, wherein the first reagent container accommodates the first reagent and comprises a first record section which contains a first reagent management information;

a second reagent container holder capable of holding a plurality of reagent containers including a second reagent container, wherein the second reagent container accommodates the second reagent and comprises a second record section which contains a second reagent management information;

at least one information reader for reading the first reagent management information from the first record section and for reading the second reagent management information from the second record section; and at least one control unit comprising a central processing unit and a memory storing computer executable program instructions, wherein when executed by the central processing unit, the computer executable program instructions cause the at least one control unit to:

determine whether a combination of the first reagent and the second reagent is usable for measurement based on the first reagent management information and the second reagent management information read by the at least one information reader;

when the combination of the first reagent and the second reagent is determined to be usable for measurement, initiate a measurement of a predetermined analysis item using the first reagent and the second reagent corresponding to the combination so as to obtain a measurement result; and process the measurement result so as to obtain an analysis result of the sample.

2. The sample analyzer according to claim 1, wherein determining whether the combination of the first reagent and the second reagent is usable for measurement includes determining whether or not the first reagent management information and the second reagent management information correspond.

3. The sample analyzer according to claim 2, wherein
the first reagent management information comprises first analysis item information,
the second reagent management information comprises second analysis item information, and
the at least one control unit determines whether or not the first analysis item information and the second analysis item information correspond.

4. The sample analyzer according to claim 2, wherein
the first reagent management information comprises first lot number information,
the second reagent management information contains second lot number information, and
the at least one control unit determines whether or not the first lot number information and the second lot number information correspond.

5. The sample analyzer according to claim 2, wherein
the first reagent management information comprises first analysis item information and first lot number information,
the second reagent management information comprises second analysis item information and second lot number information,
the at least one control unit determines whether or not the first analysis item information and the second analysis item information correspond, and whether or not the first lot number information and the second lot number information correspond, and the at least one control unit registers the combination of the first reagent and the second reagent when the at least one control unit determines that the first analysis item information and the first lot number information correspond to the second analysis item information and the second lot number information.

6. The sample analyzer according to claim 2, wherein the at least one control unit prohibits registration of the combination of the first reagent and the second reagent when the at least one control unit determines that the first reagent management information and the second reagent management information do not correspond.

7. The sample analyzer according to claim 1, wherein
the first reagent management information comprises first serial number information of the first reagent container,
the second reagent management information comprises second serial number of the second reagent container, and
the at least one control unit registers information regarding correspondence relation of the first serial number information and the second serial number information when the combination of the first reagent and the second reagent is determined to be usable for measurement.

8. The sample analyzer according to claim 1, wherein the computer executable program instructions further cause the at least one control unit to:
accept an order for measurement;
determine presence or absence of a combination of the first reagent and the second reagent for performing the measurement corresponding to the order accepted by the at least one control unit; and
prohibit measurement based on the order when the at least one control unit determines absence of the reagent combination for performing the measurement corresponding to the order accepted by the at least one control unit.

9. The sample analyzer according to claim 8, wherein the computer executable program instructions further cause the at least one control unit to warn a user that measurement based on the order is prohibited when the at least one control unit determines absence of the reagent combination for performing the measurement corresponding to the order accepted by the at least one control unit.

10. The sample analyzer according to claim 1, wherein the computer executable program instructions further cause the at least one control unit to accept specification of the reagent combination to be replaced or retrieved from a user, wherein
the first reagent container holder is configured to movably hold the first reagent container,
the second reagent container holder is configured to movably hold the second reagent container, and
when the specification of the reagent combination to be replaced or retrieved is accepted, the first reagent container holder moves the first reagent container corresponding to the first reagent forming the reagent combination to a first retrieving position where the first reagent container held by the first reagent container holder is retrieved, and the second reagent container holder moves the second reagent container corresponding to the second reagent forming the reagent combination to a second retrieving position where the second reagent container held by the second reagent container holder is retrieved.

11. The sample analyzer according to claim 10,
wherein the computer executable program instructions further cause the at least one control unit to:

control a first conveyance section for conveying the first reagent container from the first retrieving position to the outside of the first reagent container holder and control a second conveyance section for conveying the second reagent container from the second retrieving position to the outside of the second reagent container holder, wherein when the specification of the reagent combination to be replaced or retrieved is accepted, the at least one control unit controls the first conveyance section so as to convey the first reagent container corresponding to the first reagent forming the reagent combination from the first retrieving position to the outside of the first reagent container holder, and the at least one control unit controls the second conveyance section so as to convey the second reagent container corresponding to the second reagent forming the reagent combination from the second retrieving position to the outside of the second reagent container holder.

12. The sample analyzer according to claim 11, wherein when the specification of the reagent combination to be replaced is accepted, the at least one control unit controls the first conveyance section so as to convey the first reagent container arranged at a first set position on the outside of the first reagent container holder from the first set position to the first retrieving position, the first reagent container holder moves the first reagent container corresponding to the first reagent forming the reagent combination to be replaced to the first retrieving position, the at least one control unit controls the first conveyance section so as to convey the first reagent container corresponding to the first reagent forming the reagent combination to be replaced from the first retrieving position to the outside of the first reagent container holder, the at least one control unit controls the second conveyance section so as to convey the second reagent container arranged at a second set position on the outside of the second reagent container holder from the second set position to the second retrieving position, the second reagent container holder moves the second reagent container corresponding to the second reagent forming the reagent combination to be replaced to the second retrieving position, the at least one control unit controls the second conveyance section so as to convey the second reagent container corresponding to the second reagent forming the reagent combination to be replaced from the second retrieving position to the outside of the second reagent container holder.

13. The sample analyzer according to claim 10, wherein the first reagent container holder rotatably holds the first reagent container, the second reagent container holder rotatably holds the second reagent container, the first retrieving position is positioned on a rotation movement path of the first reagent container, and the second retrieving position is positioned on a rotation movement path of the second reagent container.

14. The sample analyzer according to claim 10, wherein the computer executable program instructions further cause the at least one control unit to notify the termination of replacement or retrieval of the first reagent container corresponding to the first reagent forming the reagent combination to be replaced or retrieved, and the second reagent container corresponding to the second reagent forming the reagent combination to be replaced or retrieved.

15. The sample analyzer according to claim 1, wherein the computer executable program instructions further cause the at least one control unit to control a display unit to display an arrangement state of the first reagent container and the second reagent container respectively held in the first reagent container holder and the second reagent container holder.

16. The sample analyzer according to claim 15, wherein when the reagent combination is not formed from the first reagent and the second reagent, the at least one control unit controls the display unit to display the arrangement state of the first reagent and the second reagent not forming the reagent combination distinguishable from that of a first reagent and a second reagent forming the reagent combination.

17. The sample analyzer according to claim 16, wherein the computer executable program instructions further cause the at least one control unit to allow a user to select a reagent container on the display unit displaying the arrangement of the first reagent container and the second reagent container and wherein the at least one control unit controls the display unit to display reasons the reagent containers do not form the reagent set when the first reagent or the second reagent not forming the reagent combination is selected.

18. The sample analyzer according to claim 1, wherein the at least one information reader comprises one information reader for reading the first reagent management information from the first record section and for reading the second reagent management information from the second record section.

19. The sample analyzer according to claim 1, wherein the at least one information reader comprises a first information reader for reading the first reagent management information from the first record section and a second information reader for reading the second reagent management information from the second record section.

* * * * *